US005784098A

United States Patent [19]
Shoji et al.

[11] Patent Number: 5,784,098
[45] Date of Patent: Jul. 21, 1998

[54] APPARATUS FOR MEASURING THREE-DIMENSIONAL CONFIGURATIONS

[75] Inventors: Hideyuki Shoji, Sagamihara; Shinichiro Hattori, Akishima; Masahide Kanno, Hachioji; Yasushi Namii, Hachioji; Masaru Shiraiwa, Hachioji; Kimihiko Nishioka, Hachioji; Nobuyuki Matsuura, Hino; Akira Kusumoto, Hachioji, all of Japan

[73] Assignee: Olympus Optical Co., Ltd., Tokyo, Japan

[21] Appl. No.: 655,761

[22] Filed: May 30, 1996

[30] Foreign Application Priority Data

Aug. 28, 1995 [JP] Japan .................... 7-219319

[51] Int. Cl.$^6$ .................................... H04N 7/18
[52] U.S. Cl. .................. 348/45; 348/65; 348/68; 348/139; 348/197; 356/5.01; 356/376; 359/29
[58] Field of Search ............... 348/42, 45, 47, 348/51, 61, 65–70, 77, 135, 139, 169, 197; 356/5.01, 376; 359/29

[56] References Cited

U.S. PATENT DOCUMENTS

| 4,349,277 | 9/1982 | Mundy et al. | 356/376 |
| 4,651,201 | 3/1987 | Schoolman | 348/45 |
| 4,656,508 | 4/1987 | Yokota | 348/45 |
| 4,687,326 | 8/1987 | Corby, Jr. | 356/5 |
| 4,873,572 | 10/1989 | Miyazaki et al. | 348/45 |
| 4,895,431 | 1/1990 | Tsujiuchi et al. | 359/29 |
| 4,938,205 | 7/1990 | Nudelman | 128/6 |
| 5,109,276 | 4/1992 | Nudelman et al. | 348/47 |
| 5,200,838 | 4/1993 | Nudelman et al. | 358/443 |
| 5,351,677 | 10/1994 | Kami et al. | 600/109 |
| 5,436,655 | 7/1995 | Hiyama et al. | 348/45 |

OTHER PUBLICATIONS

Kazuo Araki et al., "High Speed and Continuous 3–D Measurement System," Dec. 10, 1992, pp. 27–30.

*Primary Examiner*—Amelia Au
*Assistant Examiner*—Frank Snow
*Attorney, Agent, or Firm*—Morgan, Lewis & Bockius LLP

[57] ABSTRACT

N lines of line-shaped light are projected onto the object by means of a measuring light projecting lens. The light carrying the image of the object is passed through the eyepiece lens 17 in an endoscope 6 and the auxiliary lens 30 in a measuring head 11 and split into two beamlets by a beam splitter 31, with one beamlet being focused at a position coinciding with the entrance end faces of measuring light's position detecting fibers 33(1) to 33(m). The line-shaped light images of the object thus formed in positions coinciding with the entrance end faces of measuring light's position detecting fibers 33(1) to 33(m) are scanned linearly by those linearly aligned fibers as they are oscillated and driven by a fiber scanner 36. The scanned line-shaped light images are then subjected to the necessary signal processing in a signal processor circuit 35 such as to measure the three-dimensional configuration of the object.

87 Claims, 35 Drawing Sheets 33 (1) ~ 33 (m)

WHEN MOVING LEFTWARD     WHEN MOVING RIGHTWARD

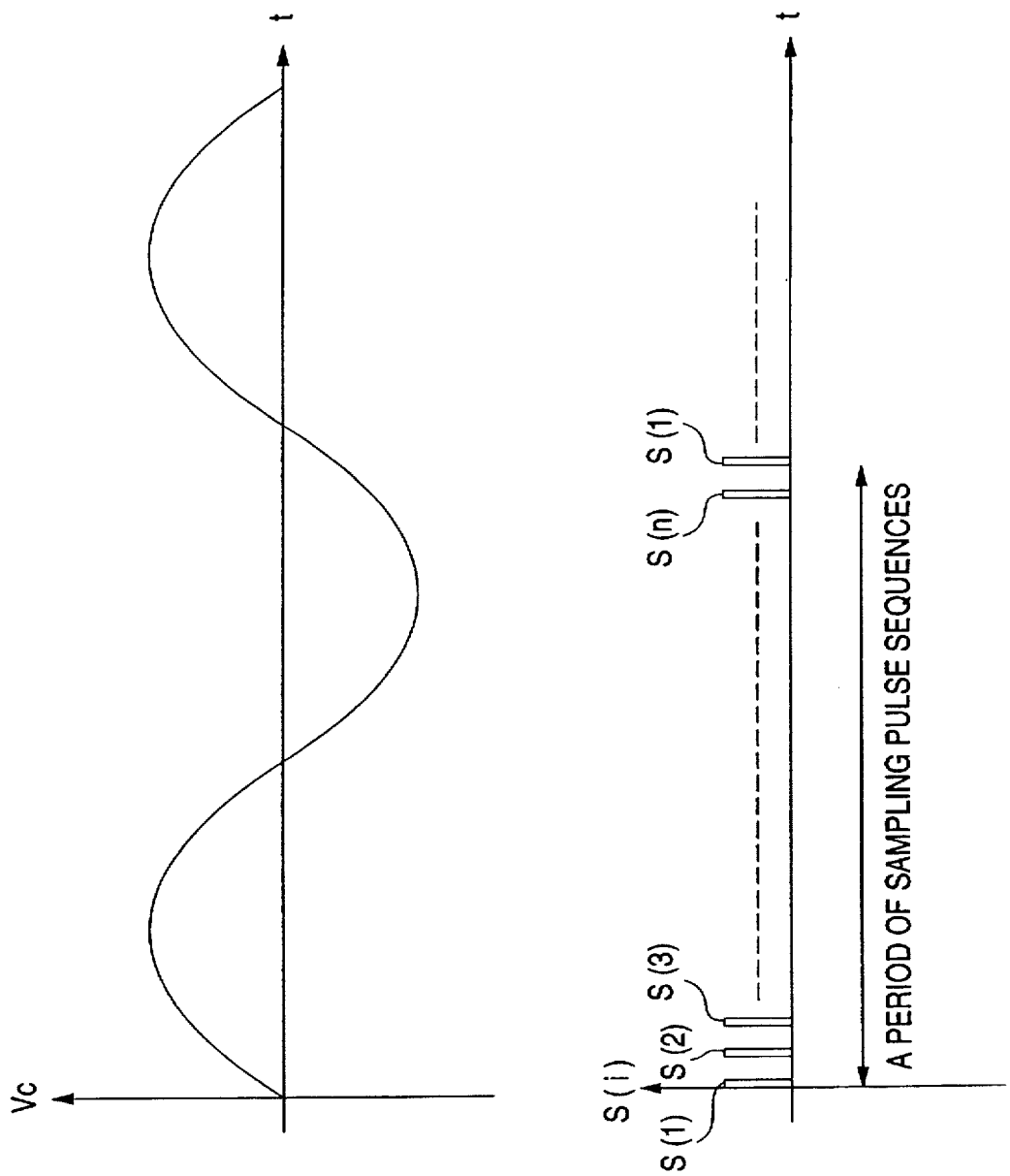

APPARATUS FOR MEASURING THREE-DIMENSIONAL CONFIGURATIONS

BACKGROUND OF THE INVENTION

The present invention relates to an apparatus for measuring three-dimensional configurations, more particularly, to an apparatus for measuring 3-D configurations that is characterized by the portion that is applied to medical endoscopes for measuring the configurations of the walls of the stomach, large intestine and other organs or applied to industrial endoscopes for measuring deformations such as in water and gas pipes, as well as the size of damage to them.

The three-dimensional configuration of an object including its surface state (i.e. high and low points) and size can be measured with measuring light that is projected onto the object. Conventionally, a laser spot is projected onto the object and the positional deviation of the spot on the object is detected for determining its tree-dimensional configuration. To measure the entire part of the object, it is necessary to perform two-dimensional scanning over the object with spot light.

Another approach that has been taken consists of projecting laser light onto an object as line-shaped slit light rather than spot light and examining the deformation of the slit light so as to calculate the surface state of the linear area illuminated with the slit light. For measuring its entire part, the object is subjected to one-dimensional scanning with the slit light.

A third approach that has been proposed consists of illuminating an object with measuring light encoded in black and white patterns of both space and time and measuring the surface state of the object in terms of the deviation of each measuring light on the object. This method is capable of measuring the entire part of the object at a time since the encoded light is flooded over the entire object.

However, these conventional methods have their own problems. In the first method which performs two-dimensional scanning of the object with a projected laser spot, only one point can be measured at a time and it takes much a prolonged time to measure the entire part of the object. Hence, a moving object defies correct measurement over the entire portion.

In the second method which performs one-dimensional scanning of the object with projected slit light, a special device is necessary to achieve simultaneous measurement of areas illuminated with the slit light, as exemplified by the two-dimensional PSD (position-sensitive device) which was proposed in Araki, Shimizu, et al., "Kosoku Renzoku Sanjigen Keisoku Shisutem (High-Speed and Continuous 3-D Measurement System)", Reference Materials for the Third Symposium on 3D Technology Study Group, pp. 27–30, Dec. 10, 1992. The use of such special devices makes the measurement a costly operation.

In the third method which illuminates the object with measuring light encoded in black and white patterns of space and time, the coding patterns will deviate if the object moves and it often becomes impossible to perform correct measurements.

SUMMARY OF THE INVENTION

The present invention has been accomplished under these circumstances and has as an object providing an apparatus for measuring three-dimensional configurations that projects many kinds of measuring (line-shaped) light onto an object simultaneously so as to ensure that the measuring speed and the resolution are improved at the same time.

The apparatus of the invention for measuring three-dimensional configurations comprises: measuring light generating means for generating more than one measuring light at different modulation frequencies; measuring light projecting means for spatially separating said more than one measuring light such that it is projected onto the surface to be measured of an object; detection means for detecting the spatial distribution of the reflected light from said surface to be measured; reflected light analyzing means for differentiating the reflected components of said more than one measuring light on the basis of said modulation frequencies with respect to the spatial distribution of the reflected light sensed by said detection means; and distance calculating means for calculating the distance between each point in said surface to be measured and said measuring light projecting means from the spatial position of each of the reflected components differentiated by said reflected light analyzing means.

In the apparatus of the invention for measuring three-dimensional configurations, the means for projecting the measuring light spatially separates the more than one measuring light from the measuring light generating means such that it is projected onto the surface to be measured of the object, and the means for analyzing the reflected light from the surface to be measured differentiates the reflected components of the more than one measuring light on the basis of the modulation frequencies with respect to the spatial distribution of the reflected light sensed by the detection means, and the distance calculating means calculates the distance between each point in the surface to be measured and the measuring light projecting means from the spatial position of each of the reflected components differentiated by the reflected light analyzing means. By this procedure, many kinds of measuring (line-shaped) light can be projected onto the object simultaneously so as to improve the measuring speed and the resolution at the same time.

BRIEF DESCRIPTION OF THE DRAWINGS

FIG. 45 is a timing chart showing the relation between carrier signal Vc and sampling pulses.

DETAILED DESCRIPTION OF THE INVENTION

Various embodiments of the invention will now be described with reference to the accompanying drawings.

Figure 1:
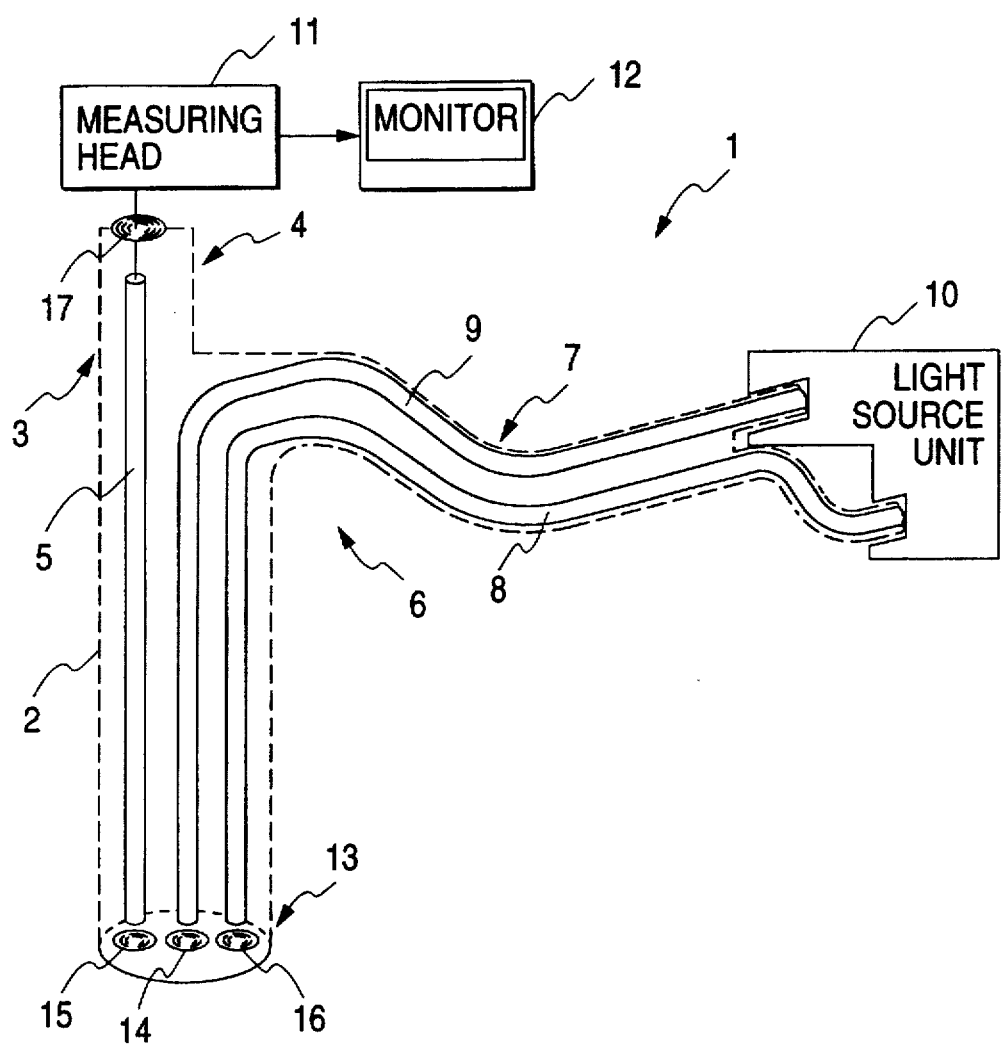
FIG. 1 shows the construction of an endoscope apparatus for measuring three-dimensional configurations according to a first embodiment of the invention.
Figure 2:
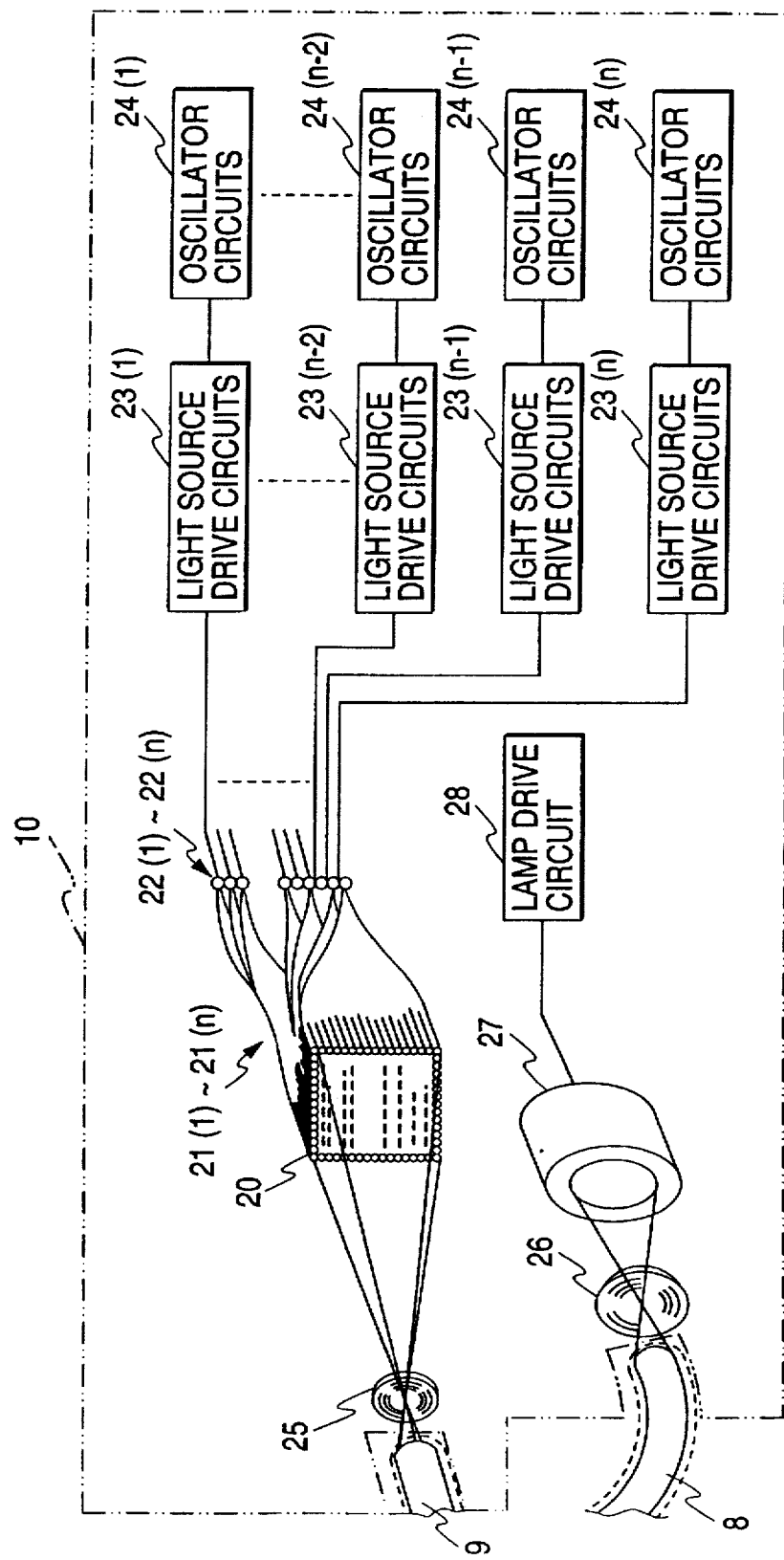
FIG. 2 shows the composition of the light source unit shown in FIG. 1.
Figure 3:
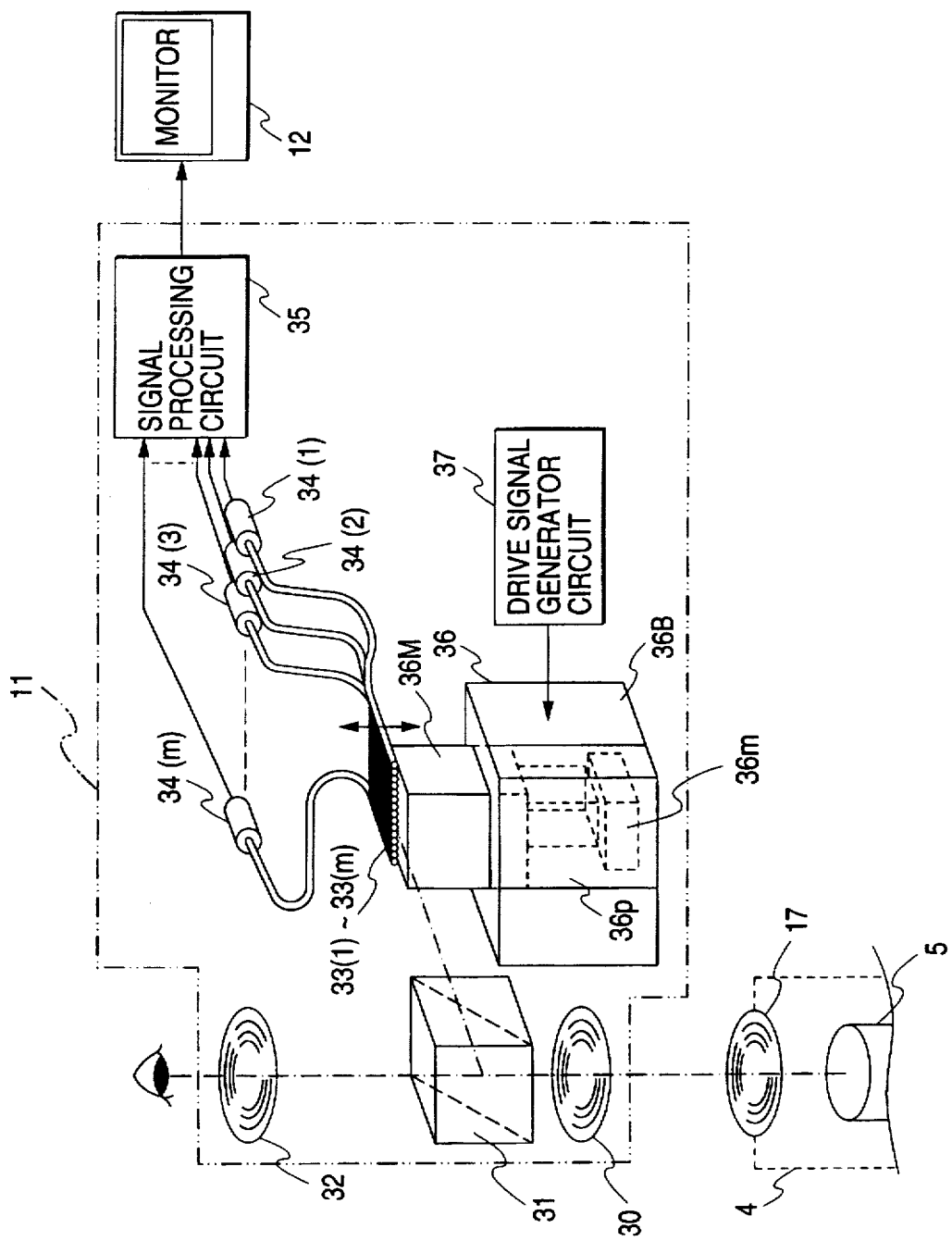
FIG. 3 shows the composition of the measuring head shown in FIG. 1.
Figure 4:
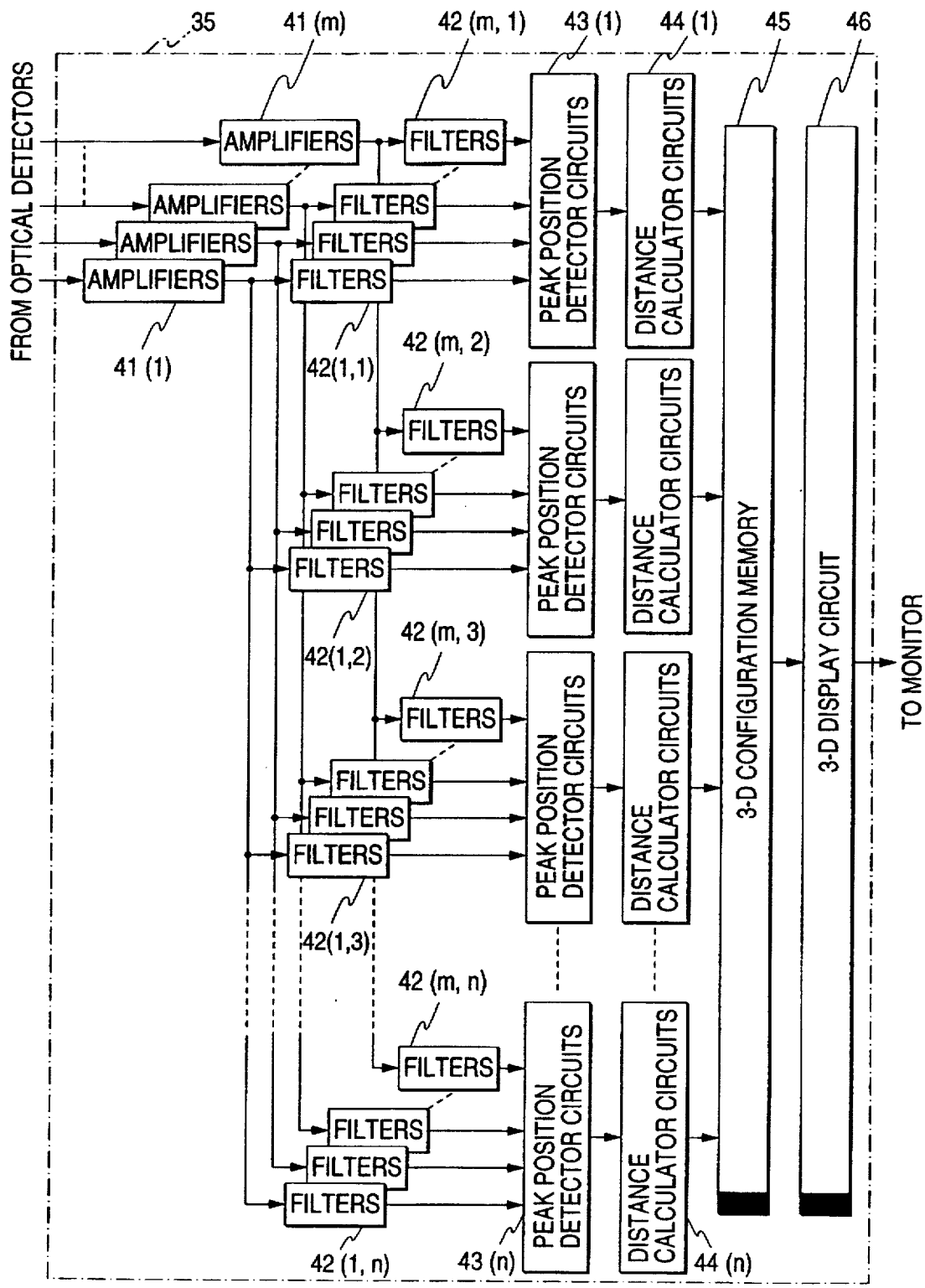
FIG. 4 shows the configuration of the signal processing circuit shown in FIG. 3.
Figure 5:
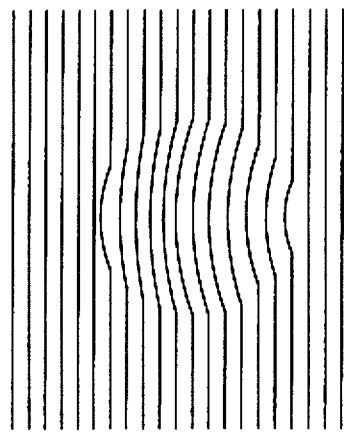
FIG. 5 illustrates n lines of line-shaped light as emitted from the measuring light transmitting image guide fiber in FIG. 1 to illuminate an object.
Figure 6:
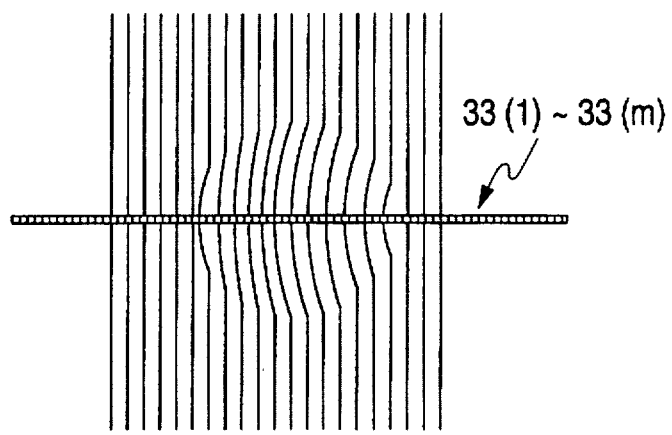
FIG. 6 illustrates how the image formed at the entrance end face of the line of measuring light's position detecting fibers in FIG. 1 relates to the n lines of line-shaped light illuminating the object.
Figure 7:
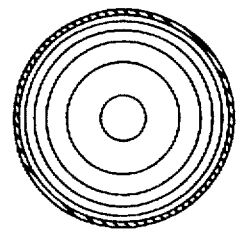
FIG. 7 illustrates a first 3-D measured image as generated with the signal processing circuit shown in FIG. 4.
Figure 8:
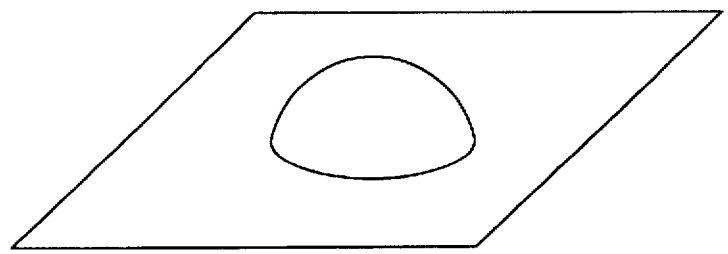
FIG. 8 illustrates a second 3-D measured image as generated with the signal processing circuit shown in FIG. 4.
Figure 9:
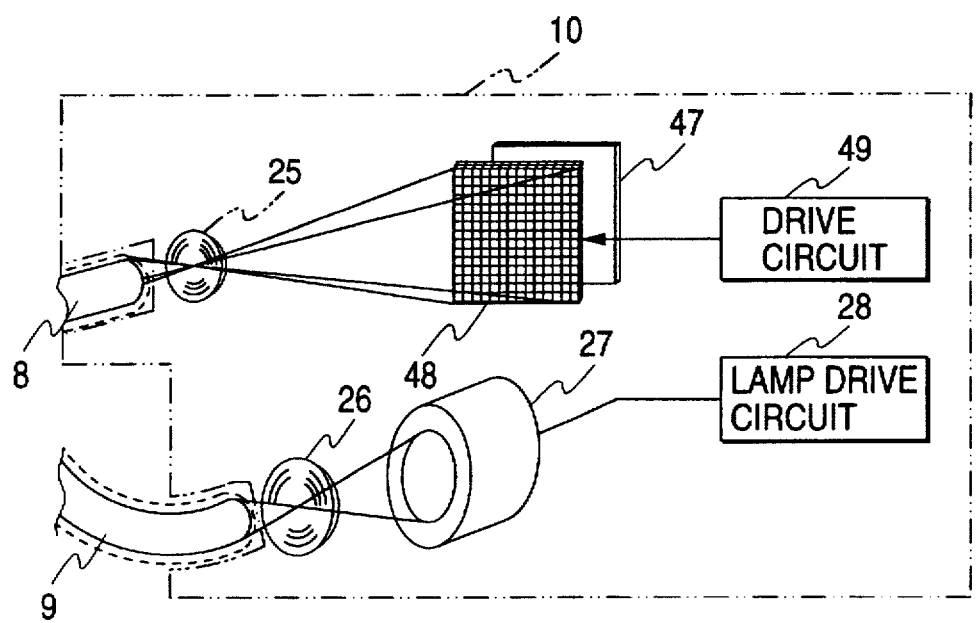
FIG. 9 shows the construction of a modified version of the light source unit shown in FIG. 1.

FIGS. 1 to 9 show the first embodiment of the invention. FIG. 1 shows the construction of an endoscope apparatus for measuring three-dimensional configurations according to the first embodiment; FIG. 2 shows the composition of the light source unit shown in FIG. 1; FIG. 3 shows the composition of the measuring head shown in FIG. 1; FIG. 4 shows the configuration of the signal processing circuit shown in FIG. 3; FIG. 5 illustrates n lines of line-shaped light as emitted from the measuring light transmitting image guide fiber in FIG. 1 to illuminate an object; FIG. 6 illustrates how the image formed at the entrance end face of the line of measuring light's position detecting fiber in FIG. 1 relates to the n lines of line-shaped light illuminating the object; FIG. 7 illustrates a first 3-D measured image as generated with the signal processing circuit shown in FIG. 4; FIG. 8 illustrates a second 3-D measured image as generated with the signal processing circuit shown in FIG. 4; and FIG. 9 shows the construction of a modified version of the light source unit shown in FIG. 1.

As shown in FIG. 1, the endoscope apparatus 1 as a device for measuring three-dimensional configurations according to the first embodiment of the invention comprises the following components; an endoscope 6 that has a portion 2 to be inserted into a canal in the human body and which has an object image transmitting image guide 5 provided within the portion 2 to ensure that both image of an object (which is located within the canal ahead of the distal end of the portion 2) and returning measuring light (to be described hereinafter) for measuring the three-dimensional configuration of the object are transmitted to an eyepiece portion 4 provided in a manipulating portion 3 coupled to the basal end of the portion 2; a light source unit 10 for supplying both illuminating light and measuring light to a universal cable 7 extending from the manipulating portion 3 of the endoscope 6, as well as to an illuminating light transmitting lightguide 8 and a measuring light transmitting image guide fiber 9 that pass through the portion 2; a measuring head 11 that is detachably fitted to the eyepiece portion 4 of the endoscope 6 and which performs both signal processing such as taking the image of the object transmitted through the image guide 5 and measuring processing of three-dimensional configurations with the returning measuring light; and a monitor 12 for displaying the image that has been subjected to signal processing with the measuring head 11.

As shown in FIG. 2, the light source unit 2 has a plurality of optical fiber bundles 21(1) to 21(n) that are gathered at the entrance end and arranged parallel to each other at the exit end to form a flat plane 20. At the entrance end, the fiber bundles 21(1) to 21(n) are aligned linearly. At the entrance end face, the fiber bundles 21(1) to 21(n) are respectively provided with n light sources 22(1) to 22(n) typically in the form of a light-emitting diode or semiconductor laser.

The light sources 22(1) to 22(n) are respectively connected to drive circuits 23(1) to 23(n) which, in turn, are connected to oscillator circuits 24(1) to 24(n) operating at different frequencies.

An imaging lens 25 is provided in front of the flat plane 20 which is composed of the end faces of fiber bundles 21(1) to 21(n). Positioned on the other side of the imaging lens 25 is an entrance end face of the measuring light transmitting image guide fiber 9.

The lightguide 8 has its entrance end face set in a face-to-face relationship with a condenser lens 26 provided in the light source unit 10. Positioned on the other side of the condenser lens 26 is a lamp 27 which, in turn, is connected to a drive circuit 28.

Turning back to FIG. 1, the distal end 13 of the insertable portion 2 of the endoscope 6 has a measuring light projecting lens 14 provided in a face-to face relationship with the exit end of the measuring light transmitting image guide fiber 9. The distal end 13 is also provided with an objective lens 15 for taking the image of the object and an illumination lens 16 for illuminating the object. One end face of the object image transmitting image guide 5 is in a face-to-face relationship with the objective lens 15, and the illuminating light transmitting lightguide 8 is in a face-to-face relationship with the illumination lens 16. The image guide 5 passes through the insertable portion 2 of the endoscope 6 until the other end of the image guide 5 comes in a face-to-face relationship with an eyepiece lens 17 in the eyepiece portion 4 within the manipulating portion 3.

As shown in FIG. 3, the measuring head 11 to be detachably fitted to the eyepiece lens 7 has an auxiliary lens 30 provided in front of the eyepiece lens 17 for focusing the light from the eyepiece lens 17; behind the auxiliary lens 30, a beam splitter 31 is provided for splitting the optical path. A second eyepiece lens 32 is provided in one of the optical paths from the beam splitter 31 for viewing enlarged the image of the object formed by the auxiliary lens 30.

The other optical path from the beam splitter 31 has end faces of linearly aligned measuring light's position detecting optical fibers 33(1) to 33(m) located in the imaging position.

The optical fibers 33(1) to 33(m) are individually separated at the other end and the respective fibers are positioned in front of optical detectors 34(1) to 34(m) which are typically composed of a photodiode or photomultiplier. The outputs of optical detectors 34(1) to 34(m) are delivered to a signal processing circuit 35.

The signal processing circuit 35 is shown more specifically in FIG. 4. The outputs of optical detectors 34(1) to 34(m) are fed into amplifiers 41(1) to 41(m) and the outputs of amplifiers 41(1) to 41(m) are fed into filters 42(x,1) to 42(x,n) (x=1, 2, . . . , m) which are bandpass filter circuits having n values of center frequency.

The outputs of filters 42(x,1) to 42(x,n) (x=1, 2, . . . , m) are fed into peak position detector circuits 43(1) to 43(n) in such a way that the outputs of the filters having the same value of center frequency are fed into the associated peak position detector circuit. The outputs of the peak position detector circuits 43(1) to 43(n) are fed into distance calculating circuits 44(1) to 44(n), the outputs of which in turn are fed into a 3-D configuration memory 45. The output of the 3-D configuration memory 45 is connected to the monitor 12 via a 3-D display circuit 46.

Turning back to FIG. 3, the linearly aligned end faces of the measuring light position detecting fibers 33(1) to 33(n) are secured to a fiber scanner 36 which is typically composed of a voice coil or a piezoelectric device and which is connected to a drive signal generator circuit 37 which generates a drive signal in synchronism with the sync signal to the monitor 12.

The endoscope apparatus 1 which is thus constructed operates as follows to measure three-dimensional configurations.

Oscillator circuits 24(1) to 24(n) oscillate sine waves at different frequencies, which are sent to light source drive circuits 23(1) to 23(n). These drive circuits apply a dc bias to the received signals and use them to drive light sources 22(1) to 22(n), which then emit light that is intensity-modulated by the sine waves at different frequencies.

The emitted light is launched into the gathered end faces of the optical fiber bundles 21(1) to 21(n), which then emit n lines of line-shaped light from the linearly aligned other end faces (strictly speaking, the line-shaped light consists of points of light in a row but the dark areas between adjacent points of light may be eliminated by a light diffusing plate or some other light diffusing means that are provided at the exit end faces).

The emerging n lines of line-shaped light are focused by the imaging lens 25 to form a reduced image at one end face of the measuring light transmitting image guide fiber 9. The thus processed n lines of line-shaped light which consist of different frequency components at respective intensities are transmitted through the image guide fiber 9 to emerge from the other end face which coincides with the distal end 13 of the insertable portion 2 of the endoscope 6.

The emerging line-shaped light is projected onto the object through the measuring light projecting lens 14. The projected n lines of line-shaped light change in shape as shown in FIG. 5 in accordance with the surface state (i.e. high and low points) of the object.

The line-shaped light thus projected onto the object is reflected from the latter and passed through the objective lens 15 to be focused to form an image at the end face of the object image transmitting image guide 5. The image is transmitted through the image guide 5 to reach the other end which is located in the manipulating portion 3 of the endoscope 6.

The light reaching the other end of the image guide 5 is passed through the eyepiece lens 17 and the auxiliary lens 30 in the measuring head 11 and split into two beamlets by the beam splitter 31, with one beamlet being focused at a position coinciding with the entrance end faces of measuring light position detecting fibers 33(1) to 33(m). As shown in FIG. 6, the line-shaped light images of the object are formed in such a way that their length crosses at substantially right angles with the row of measuring light's position detecting fibers 33(1) to 33(m).

The other beamlet emerging from the beam splitter 31 is focused ahead of the second eyepiece lens 32 and the resulting image is enlarged by the latter so that it can be seen by the viewer.

The line-shaped light images of the object thus formed in positions coinciding with the end faces of the measuring light's position detecting fibers 33(1) to 33(m) are scanned linearly by these linearly aligned fibers as they are vibrated and driven by the fiber scanner 36.

The light launched into the fibers 33(1) to 33(m) at one end face travels through those fibers and emerge from the other end to be admitted into the optical detectors 34(1) to 34(m). As a result, the outputs from the optical detectors 34(1) to 34(m) have certain frequency components that are more intense than the other frequency components.

It should be noted here that the principal object to be viewed with the endoscope 6 is part of a living body that is small and surrounded by walls so that internal reflections of light will occur in this limited area. Hence, a particular position in the object has not only the intended measuring line-shaped light projected but also the overlapping indirect reflections of line-shaped light. This is why the light of a single line-shaped light image alone will not be admitted into the optical detectors 34(1) to 34(m). It should also be mentioned here that the indirect light is attenuated to have a small intensity relative to the intentionally projected line-shaped light.

The outputs of optical detectors 34(1) to 34(m) are amplified by amplifiers 41(1) to 41(m) in the signal processing circuit 35 and have their frequency components separated by filters 42(x,1) to 42(x,n) (x=1, 2, . . . , m). Thereafter, the intensity distributions of the outputs from the filters 42(x,1) to 42(x,n) (x=1, 2, . . . , m) are analyzed by peak position detector circuits 43(1) to 43(n) in such a way that the filters having the same value of center frequency are coupled to the associated detector circuit.

As a result, one of the optical detectors 34(1) to 34(m) is identified that outputs a signal of maximum intensity for a certain frequency component. This is equivalent to recognizing how a plurality of lines of line-shaped light as projected onto the object have changed in position in accordance with the surface state of the object.

This change (deviation) as sensed by the measuring light's position detecting fibers 33(1) to 33(m) is processed by distance calculator circuits 44(1) to 44(n) such that it is converted to the distance between the distal end of the endoscope 6 and the corresponding point on the object, which distance is subsequently stored in the 3-D configuration memory 45. What is to be stored in the 3-D configuration memory 45 is part of the image as sensed by the measuring light's position detecting fibers 33(1) to 33(m), namely, the distance data for linear regions of the object.

Subsequently, the fiber scanner 36 which is securely mounted to the underside of the measuring light's position detecting fibers 33(1) to 33(m) is operated to shift these fibers by a small distance and the same procedure as described above is repeated. This procedure will now be described in detail.

The moving body 36M on the fiber scanner 36 has a stacked piezoelectric device (PZT) 36P secured at one end such that it will extend or contract in the axial direction parallel to the direction of lamination. The other end of the piezoelectric device 36P is secured to an inertial body 36M having a greater mass than moving body 36M. Needless to say, the moving body 36m, combined with fibers 33(1) to 33(m) to provide an integral unit that effectively functions as a moving body, has a greater mass than the inertial body 36m. Electrodes on the piezoelectric device 36P are connected via leads to the drive signal generator circuit 37.

When the piezoelectric device 36P is supplied with a voltage of a specified waveform, it will either extent or contract in the axial direction to displace the moving body 36M, thereby performing linear scanning to move the fibers 33(1) to 33(m).

Figure 43:
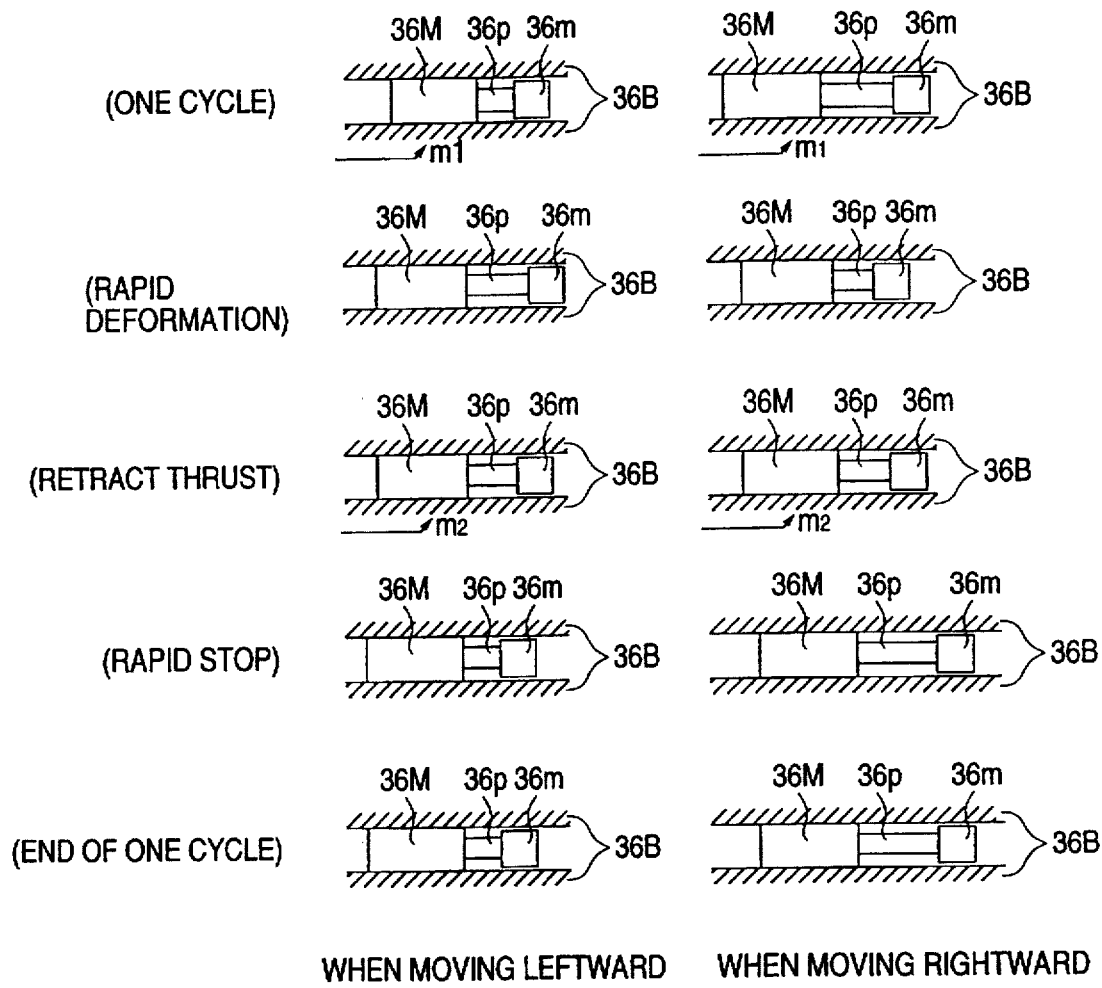
FIG. 43 shows the internal structure of the fiber scanner of the invention as it is places sideways for illustrating the principle of the movement of a moving body.
Figure 44:
FIG. 44 is another illustration of the principle behind the movement of a moving body in terms of the waveform of a drive voltage applied to a piezoelectric device.

The principle of this movement is shown conceptually in FIGS. 43 and 44. In FIG. 43, the internal structure of the fiber scanner 36 is shown for illustrative purposes as it is placed sideways. As shown, moving body 36M of a greater mass is coupled to inertial body 36m of a smaller mass by stacked piezoelectric device 36P to compose a running actuator, which is enclosed in a base 36B. When piezoelectric device 36P is supplied with drive voltages of the waveforms shown in FIG. 44, the entire part of the running actuator will either advance or retrace.

The operation for the advancing motion (to the left in FIG. 43) is first described. As shown in the top left diagram of FIG. 43, moving body 36M is held in the base 36B by a static frictional force before the necessary operation is started so that the piezoelectric device 36P is in a contracted state. As a result, the inertial body 36m is in a standby position with it being pulled close to the moving body 36M ahead.

If the piezoelectric device 36P is supplied with a high drive voltage momentarily, it will extend abruptly, causing the moving body 36M and the inertial body 36m to be displaced simultaneously in opposite directions. On this occasion, the moving body 36M is displaced in a forward direction by a distance of $\Delta m_1$ under the action of a kinetic frictional force.

Subsequently, the voltage being applied to the piezoelectric device 36P is reduced at a comparatively slow rate to contract it so that the inertial body 36m is pulled back toward the moving body 36M at a given acceleration. On this occasion, the voltage applied to the piezoelectric device 36P is adjusted to such a value that the inertial force due to the acceleration is smaller than the static frictional force between the moving body 36M and the base 36B so as to ensure that the moving body 36M comes to a rest by being retained under said static frictional force.

When the piezoelectric device 36P has been contracted fully, the application of the voltage is stopped abruptly so that the inertial body 36m will suddenly stop moving, namely, the operation of pulling back the inertial body 36m is discontinued abruptly. Then, the inertial body 36m will impinge against the moving body 36M, whereupon the fiber scanner 36 taken as a whole will outdo the above-mentioned frictional force and starts to advance. The advancing motion of the scanner 36 will continue until it stops when its kinetic energy is lost by the kinetic frictional force on the moving body 36M. This motion causes a forward displacement by a distance of $\Delta m_2$.

Thus, one cycle of this operation permits an advancement (fine movement) over a distance of $\Delta m_1 + \Delta m_2$. By repeating this fine movement in the forward direction, a great advancement of the fiber scanner 36 can be achieved.

For retraction (to the right in FIG. 43), the operating cycle described in the preceding paragraphs is reversed. Stated more specifically, as shown in the top right diagram of FIG. 43, moving body 36M is held in the base 36B by a frictional force before the necessary operation is started, so that the piezoelectric device 36P is in an extended state. As a result, the inertial body 36m is remote from the moving body 36M ahead.

If the high voltage to the piezoelectric device 36P is removed momentarily, the device will contract abruptly, whereupon the inertial force of the inertial body 36m becomes greater than the frictional force on the moving body 36M, causing both bodies to be displaced simultaneously in opposite directions. On this occasion, the moving body 36M is displaced backward by a distance of $\Delta m_1$.

Subsequently, the voltage to the piezoelectric device 36P is increased progressively to extend it so that the inertial body 36m is retracted away from the moving body 36M at a given acceleration. On this occasion, the inertial force due to the acceleration is adjusted to be smaller than the frictional force between the moving body 36M and the base 36B so as to ensure that the moving body 36M comes to a rest by being retained under said frictional force.

When the piezoelectric device 36P has been extended fully, the motion of the inertial body 36m is stopped abruptly, whereupon a great inertial force develops and the fiber scanner 36 taken as a whole will outdo the above-mentioned frictional force and starts to retract. The retracting motion of the scanner 36 will continue until it stops when its kinetic energy is lost by the kinetic frictional force on the moving body 36M. This motion causes a backward displacement by a distance of $\Delta m_2$.

Thus, one cycle of this operation permits a retraction over a distance of ($\Delta m_1 + \Delta m_2$). By repeating this fine movement in the backward direction, a great retraction of the fiber scanner 36 can be achieved.

If desired, two instances of voltage outputting may be combined to permit one cycle of scanner movement such that a drop in voltage is immediately followed by a voltage rise, whereby the energy created upon rapid deformation is added to the movement during a subsequent rapid deformation so as to produce a greater momentum.

This is the principle by which the moving body 36M can be moved back and forth, causing vertical vibrations of the fibers 33(1) to 33(n) which are coupled to the moving body 36M.

It should, however, be noted that the memory addresses for storing the distance data in the 3-D configuration memory 45 are shifted in accordance with the movement of the measuring light's position detecting fibers 33(1) to 33(m). As a result, the 3-D configuration memory 45 will eventually store the three-dimensional configuration of the object over the range to be measured.

The contents of the 3-D configuration memory 45 are processed by the 3-D display circuit 46 so that they are transformed to a bird's eye view (see FIG. 7) or a contour map (FIG. 8) or any other suitable form of data such as a height-dependent pseudo-color image, which are then displayed on the monitor 12.

The operation of distance calculation with distance calculator circuits 44(1) to 44(n) may proceed as follows. A proofing flat plate is provided and put as an object in front of the objective lens. The line-shaped light projected through the measuring light projecting lens 14 is projected in specified positions on the flat plate that are determined by the distance from the distal end of the endoscope 6 to the flat plate. In the absence of high and low points in the flat plate, the line-shaped light projected onto said plate remains linear. When the projected line-shaped light is focused by the objective lens 15 to form an image at one end face of the object image transmitting image guide 5, the respective lines of the line-shaped light on the imaging surface have their positions determined uniquely by the distance between the distal end of the endoscope and the proofing flat plate.

The positions of these lines of line-shaped light have a one-to-one correspondence to the focus positions of the lines of line-shaped light that coincide with the end faces of the measuring light's position detecting fibers 33(1) to 33(m) in the measuring head 11.

In the next step, the distance between the proofing flat plate and the distal end of the endoscope is varied. For each value of the distance, the positions of the respective lines of line-shaped light that correspond to the measuring light's position detecting fibers 33(1) to 33(m), namely, the optical detectors 34(1) to 34(m) that output signals containing the greatest amount of frequency components corresponding to those lines of line-shaped light, are formulated in a lookup table and stored in a suitable device such as a ROM or a power-backed up RAM. In actual measurement, the operator recognizes which of the optical detectors 34(1) to 34(m) delivers an output signal containing a maximum amount of frequency component associated with a certain line of line-shaped light and he then references the lookup table to calculate the distance from the distal end of the endoscope to the corresponding line of line-shaped light on the object.

Thus, with the endoscope apparatus 1 for measuring three-dimensional configurations according to the fist embodiment of the invention, n lines of line-shaped light from the optical fiber bundles 21(1) to 21(n) are projected onto the object through the measuring light projecting lens 14 and the line-shaped light images formed in positions coinciding with the end faces of the measuring light's position detecting fibers 33(1) to 33(m) are scanned linearly by these linearly aligned fibers as they are oscillated and driven by the fiber scanner 36, and the resulting signals are processed in the signal processing circuit 35 to perform three-dimensional measurement. In this way, many kinds of measuring (line-shaped) light can be projected simultaneously onto the object so as to improve the measuring speed and the resolution at the same time.

If desired, the optical fiber bundles 21(1) to 21(n), light sources 22(1) to 22(n), light source drive circuits 23(1) to 23(n) and oscillator circuits 24(1) to 24(n) in the light source unit 10 may be replaced with the system shown in FIG. 9 which comprises a surface illuminant 47, a spatial optical modulator 48 provided in front of the surface illuminant 47, and a drive circuit 49 for driving the optical modulator 48 may be adapted to be optically conjugated with the measuring light transmitting image guide fiber 9 and frequency-modulated with the drive circuit 49 for successive vertical lines, thereby producing slit light having a plurality of frequencies.

Figure 10:
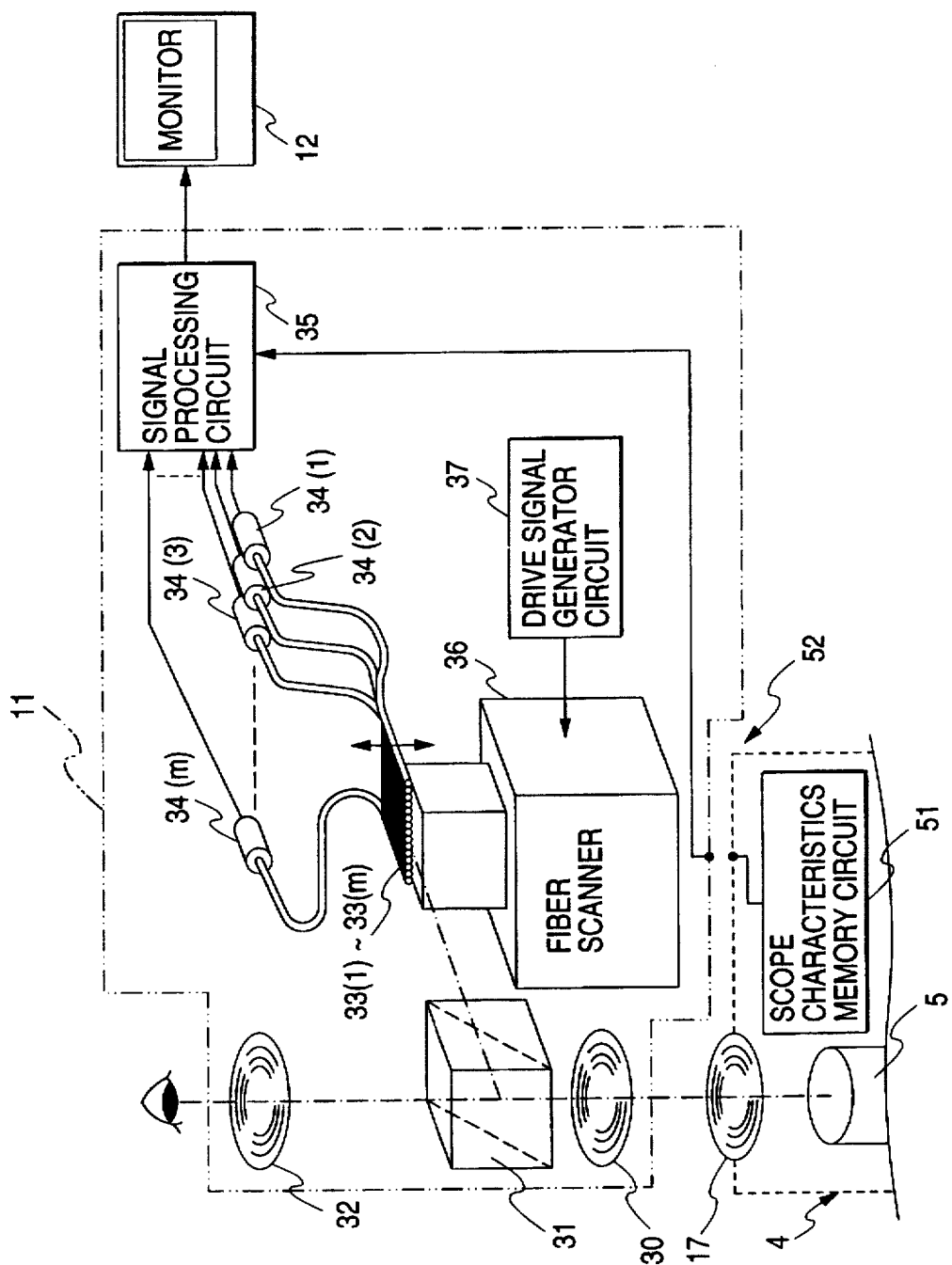
FIG. 10 shows the construction of the essential parts of an endoscope and a measuring head according to a second embodiment of the invention.
Figure 11:
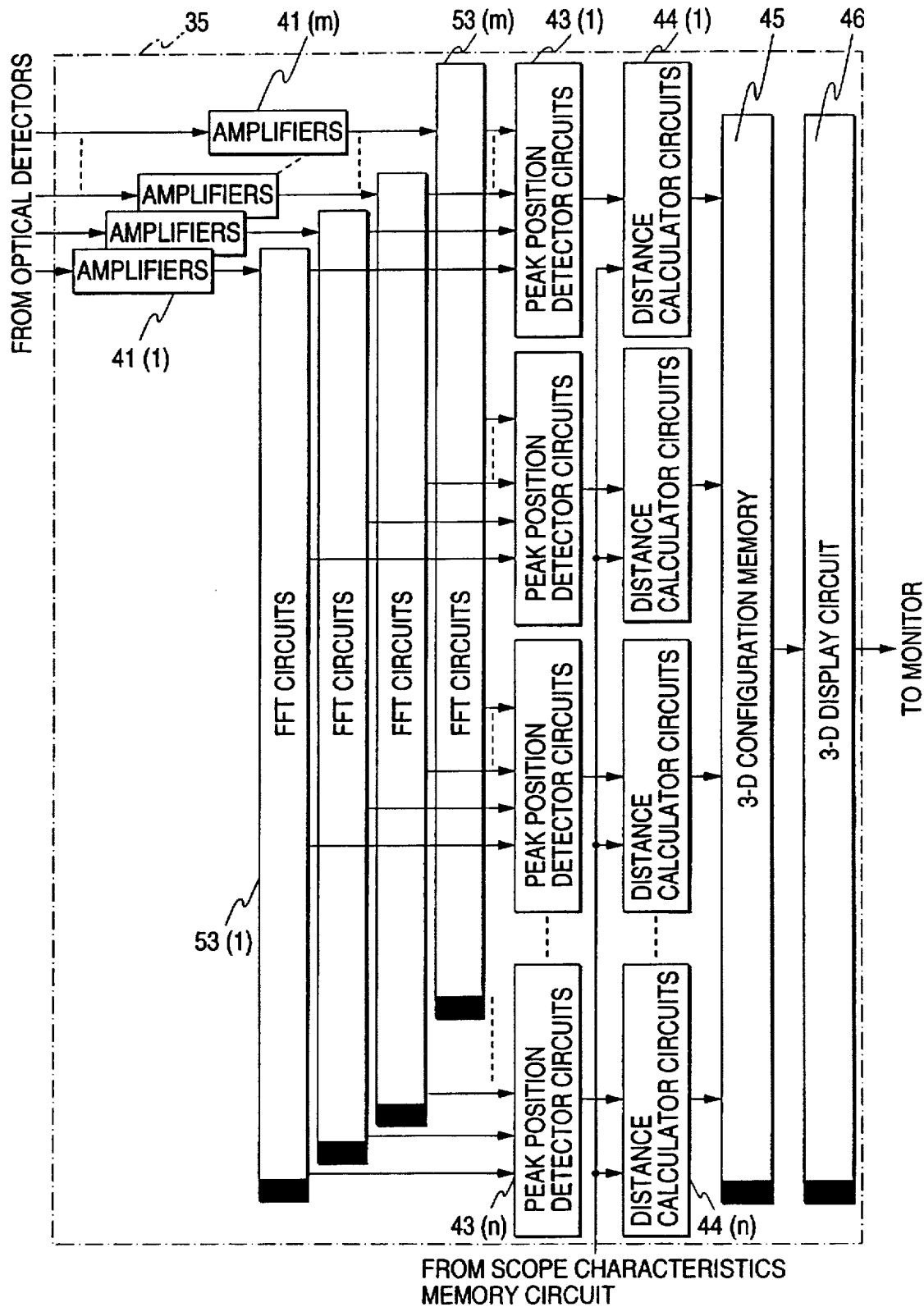
FIG. 11 shows the configuration of the signal processing circuit shown in FIG. 10.

We now describe the second embodiment of the invention with reference to FIGS. 10 and 11, in which FIG. 10 shows the construction of the essential parts of an endoscope and a measuring head according to the second embodiment and FIG. 11 shows the configuration of the signal processing circuit shown in FIG. 10.

The second embodiment is essentially the same as the first embodiment, so the following description concerns only the differences between the two embodiments and the components which are common to both embodiments are identified by like numerals and will not be described in detail.

As shown in FIG. 10, the endoscope 6 according to the second embodiment incorporates a scope characteristics memory circuit 51 which is typically composed of a programmable ROM and the output of this circuit is fed to distance calculating circuits 44(1) to 44(n) in the signal processor circuit 35 within the measuring head 11 via an eyepiece connector 52 provided in the eyepiece portion 4.

The scope characteristics memory circuit 51 stores not only the data on the distortion of the measuring light projecting lens 14 and the objective lens 15 but also the distance between the two lenses, image magnifying power of the eyepiece lens 17 and other data which, when distances are calculated by distance calculating circuits 44(1) to 44(n) in the measuring head 11, are to be referenced for correction purposes in accordance with the specifications of the endoscope 6 and manufacturing fluctuations.

The signal processing circuit 35 in the second embodiment does not have filters 42(x,1) to 42(x,n) (x=1, 2, . . . , m) but as shown in FIG. 11, FFT circuits 53(1) to 53(m) which are typically composed of a digital signal processor (DSP) to perform fast Fourier transform are substituted and connected to amplifiers 41(1) to 41(m).

The outputs of FFT circuits 53(1) to 53(m) are delivered to peak position detector circuits 43(1) to 43(n) which are typically composed of comparators. The outputs of the peak position detector circuits 43(1) to 43(n) are connected to distance calculator circuits 44(1) to 44(n) which are typically composed of a flash ROM.

The other structural aspects of the second embodiment are identical to the first embodiment.

As will be understood from the foregoing description, the second embodiment differs from the first embodiment in that FFT circuits 53(1) to 53(m) rather than filters 42(x,1) to 42(x,n) (x=1, 2, . . . , m) identify which of the optical detectors 34(1) to 34(m) issues a signal having the highest intensity of a certain frequency component. Stated more specifically, the outputs of amplifiers 41(1) to 41(m) are respectively processed with FFT circuits 53(1) to 53(m) for separating their frequency components and then fed to the peak position detector circuit 43(1) to 43(n) in such a way that the outputs of the same frequency component are supplied to the associated detector circuit. The frequency components to be separated are set at the same values as the operating frequencies of the oscillator circuits 24(1) to 24(n) in the light source unit 10.

Peak position detector circuits 43(1) to 43(n) receive a plurality of signals of the same frequency component and detect the most intense signal. In other words, there is identified one of the amplifiers 41(1) to 41(m), or optical detectors 34(1) to 34(m), that issues the most intense signal with respect to the frequency component of interest.

This is equivalent to detecting how much of the line-shaped light that is projected onto the object and which is subjected to imaging with the measuring light's position detecting fibers 33(1) to 33(m) has been deviated in position by the surface state (high and low points) of the object.

By detecting the peak position of each frequency component, the surface state of the object in the area being imaged with the measuring light's position detecting fibers 33(1) to 33(m) can be measured.

The data in the scope characteristics memory circuit 51 incorporated in the endoscope 6 are sent to the measuring head 11 via the eyepiece connector 52 and used for data correction in the process of distance measurement by means of the distance measuring circuits 44(1) to 44(n).

Alternatively, a lookup table describing the relationship between the deviation of line-shaped light on the object and the distance may be stored in the scope characteristics memory circuit 51 such that a particular distance is calculated by merely referencing the table in the process of operation in the distance calculating circuits 44(1) to 44(n).

The other operational features of the second embodiment are identical to the first embodiment. In the second embodiment, the advantages of the first embodiment are of course attained and, in addition, high precision is assured since distance correction is performed with the data in the scope characteristics memory circuit 51.

Figure 12:
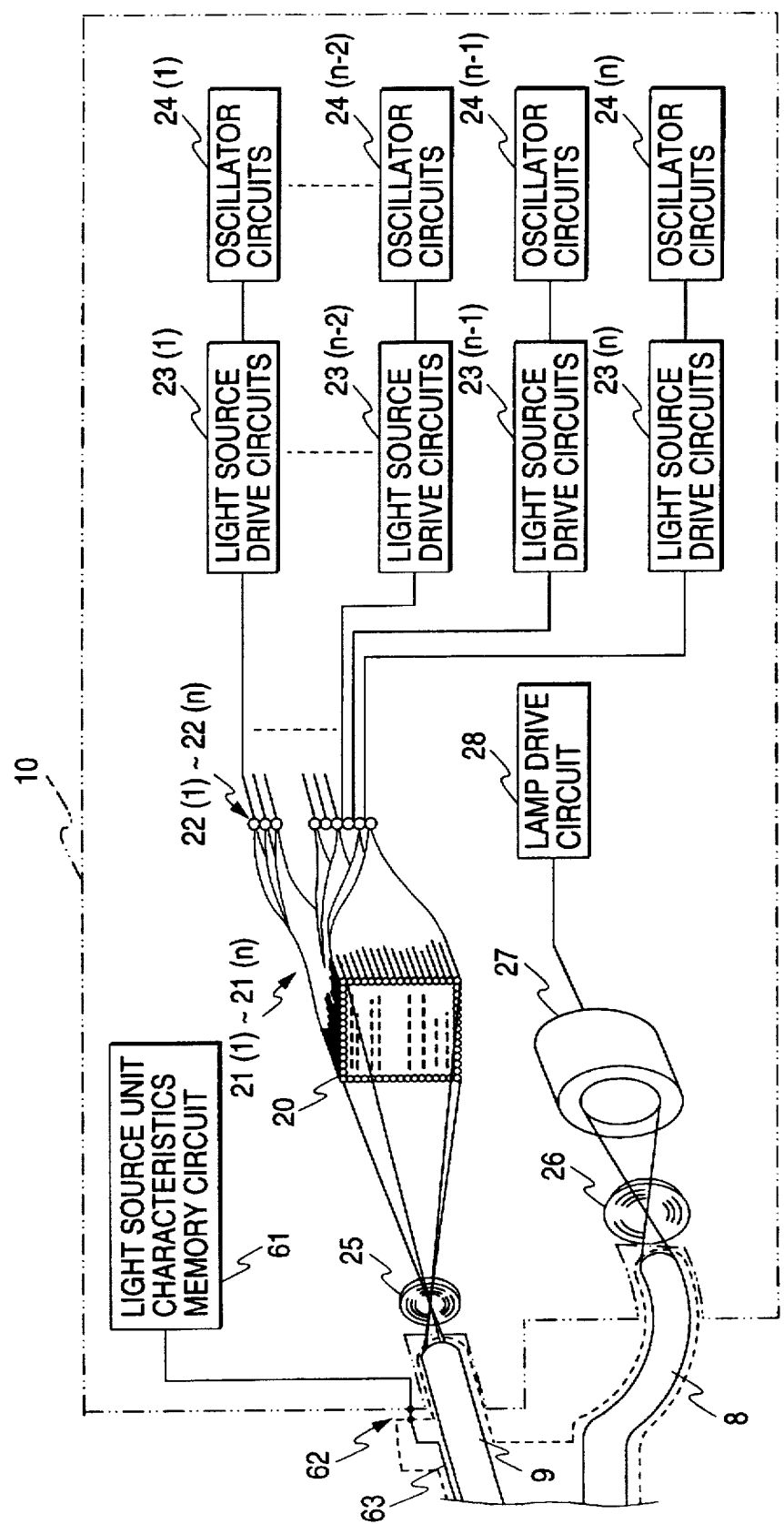
FIG. 12 shows the construction of a light source unit according to a third embodiment of the invention.
Figure 13:
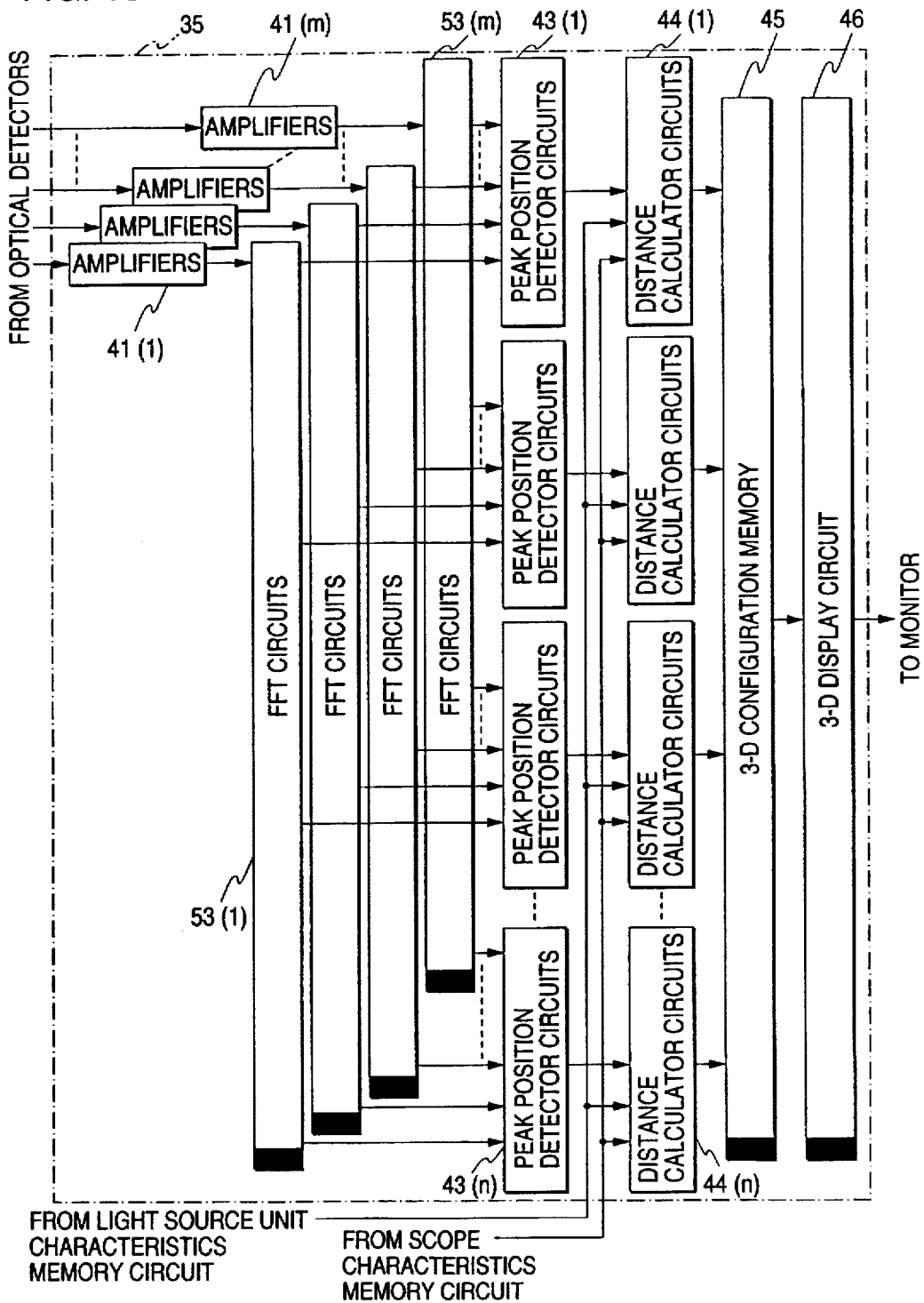
FIG. 13 shows the configuration of a signal processing circuit in a measuring head which is to be supplied via a signal cable with the output of the light source unit characteristics memory circuit shown in FIG. 12.

We now describe the third embodiment of the invention with particular reference to FIGS. 12 and 13, in which FIG. 12 shows the construction of a light source unit according to the third embodiment and FIG. 13 shows the configuration of a signal processing circuit in a measuring head which is to be supplied via a signal cable with the output of the light source unit characteristics memory circuit shown in FIG. 12.

The third embodiment is essentially the same as the second embodiment, so the following description concerns only the differences between the two embodiments and the components which are common to both embodiments are identified by like numerals and will not be described in detail.

In addition to the components used in the second embodiment, the light source unit according to the third embodiment which is indicated by 10 in FIG. 12 includes a light source unit characteristics memory circuit 61 for storing the data on fluctuations in the unit 10 such as for the light sources 22(1) to 22(n), optical fiber bundles 21(1) to 21(n) and imaging lens 25, as well as an electrical connector 62 and a signal cable 63. The signal cable 63 is passed through the endoscope 6 to be connected to the eyepiece connector 52. As shown in FIG. 13, the output of the light source unit characteristics memory circuit 61 is connected to distance calculating circuits 44(1) to 44(n) signal processing circuit 35 within the measure head 11.

The other structural aspects of the third embodiment are identical to the second embodiment.

The data on the characteristics of the light source unit 10 which are stored in the light source unit characteristics memory circuit 61 are sent to the distance calculating circuits 44(1) to 44(n) via the electrical connector 62, signal cable 63 and eyepiece connector 52 and used for data correction in the process of distance calculation.

The other operational features of the third embodiment are the same as the second embodiment. In the third embodiment, the advantages of the second embodiment are of course attained and, in addition, a higher precision is assured since distance correction is performed with the both the data in the scope characteristics memory circuit 51 and the data in the light source unit characteristics memory circuit 61.

Figure 14:
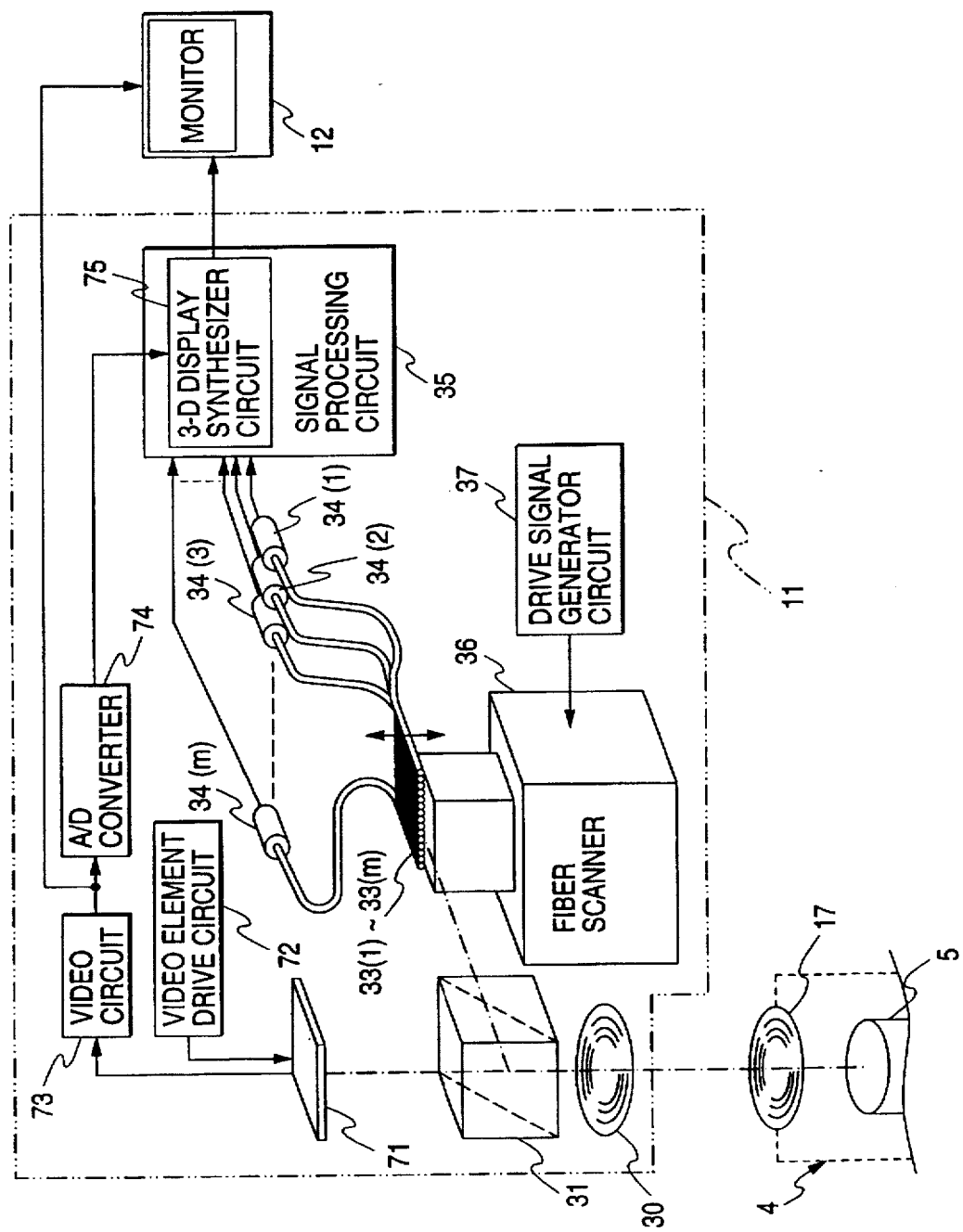
FIG. 14 shows the construction of the essential parts of an endoscope and a measuring head according to a fourth embodiment of the invention.
Figure 15:
FIG. 15 illustrates a 2-D image of an object as produced with the imaging device shown in FIG. 14.
Figure 16:
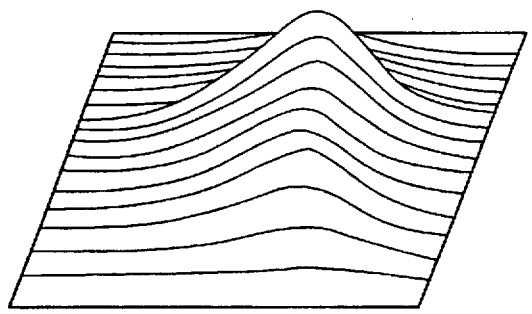
FIG. 16 illustrates a 3-D image as produced with the 3-D display synthesizer circuit shown in FIG. 14.
Figure 17:
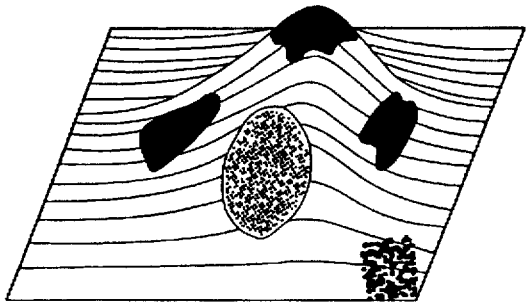
FIG. 17 illustrates a 3-D synthetic image as produced with the 3-D display synthesizer circuit shown in FIG. 14.

We next describe the fourth embodiment of the invention, with reference to FIGS. 14 to 17, in which: FIG. 14 shows the construction of the essential parts of an endoscope and a measuring head according to the fourth embodiment; FIG. 15 illustrates a 2-D image of an object as produced with the imaging device shown in FIG. 14; FIG. 16 illustrates a 3-D image as produced with the 3-D display synthesizer circuit shown in FIG. 14; and FIG. 17 illustrates a 3-D synthetic image as produced with the 3-D display synthesizer circuit shown in FIG. 14.

The fourth embodiment is essentially the same as the first embodiment, so the following description concerns only the differences between the two embodiments and the components which are common to both embodiments are identified by like numeral and will not be described in detail.

As shown in FIG. 14, the measuring head indicated by 11 does not have the second eyepiece lens 32 used in the first embodiment but an imaging device 71 typically in the form of a CCD, an imaging device drive circuit 72, a video circuit 73 and an analogue-to-digital converter (hereinafter referred to as A/D converter) 74 are substituted. The output of A/D converter 74 is delivered to the signal processing circuit 35 which is adapted to receive the output of A/D converter 74 into a 3-D display synthesizer circuit 75 substituted for the 3-D display circuit 46 used in the first embodiment.

The other structural aspects of the fourth embodiment are identical to the first embodiment.

The image of the object as split by beam splitter 31 is taken with the imaging device 71 which is driven with the drive circuit 72 and the image thus taken is processed into a video signal by means of the video circuit 73. The video signal is displayed on the monitor 12 as a 2-D endoscopic image (see FIG. 15).

The video signal is also fed into the A/D converter 74 for conversion to a digital signal which, in turn, is supplied to the 3-D display synthesizer circuit 75. In the 3-D display synthesizer circuit 75, the signal sent from the 3-D configuration memory 45 is either processed for delivery to the monitor 12 on which it is displayed as a representation of 3-D image (see FIG. 16) or synthesized with the digital signal from the A/D converter 74 to produce a composite image that is selectively displayed on the monitor 12 (see FIG. 17).

The other operational features of the fourth embodiment are the same as in the first embodiment. In the fourth embodiment, the advantages of the first embodiment are of course attained and, in addition, more reliable diagnosis can be performed since viewing is possible not only by 3-D representation but also by 2-D representation, as well as by composite representation.

Figure 18:
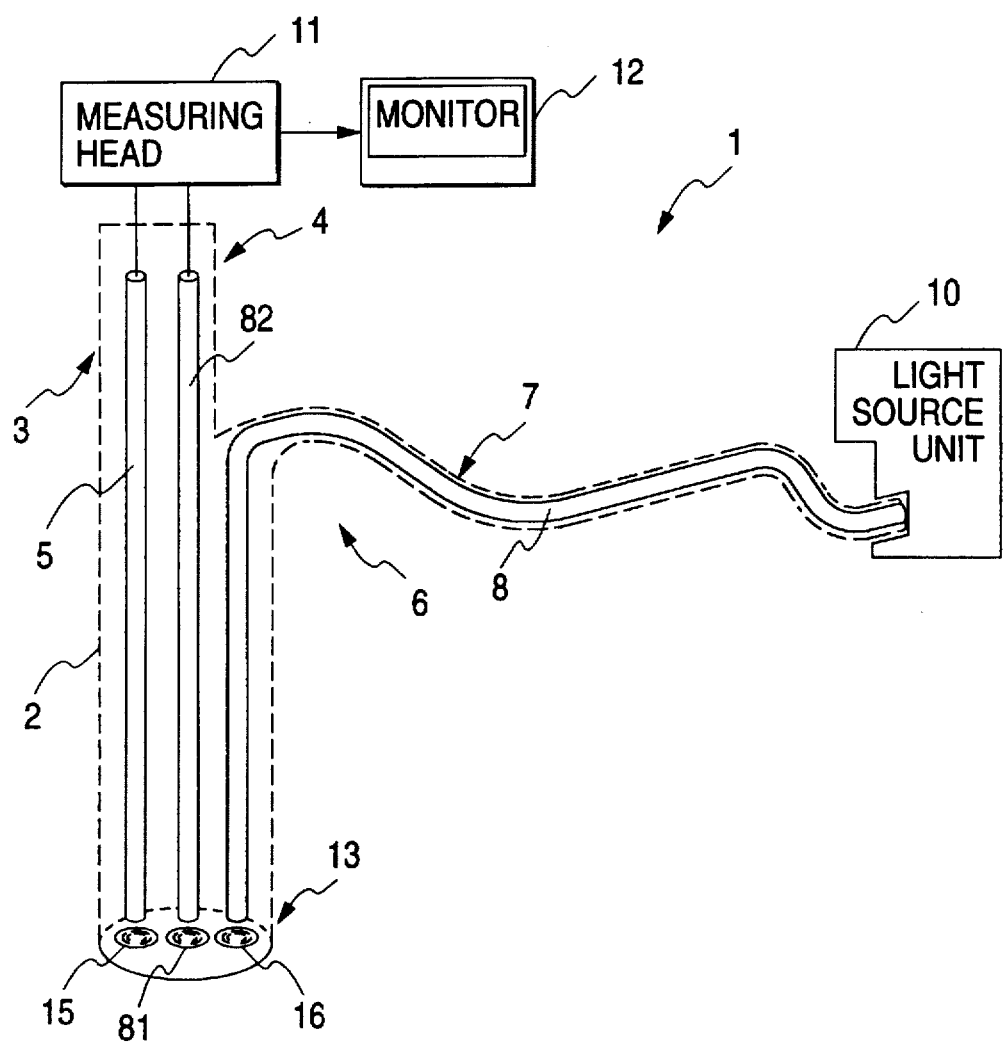
FIG. 18 shows the construction of an endoscope apparatus for measuring three-dimensional configurations according to a fifth embodiment of the invention.
Figure 19:
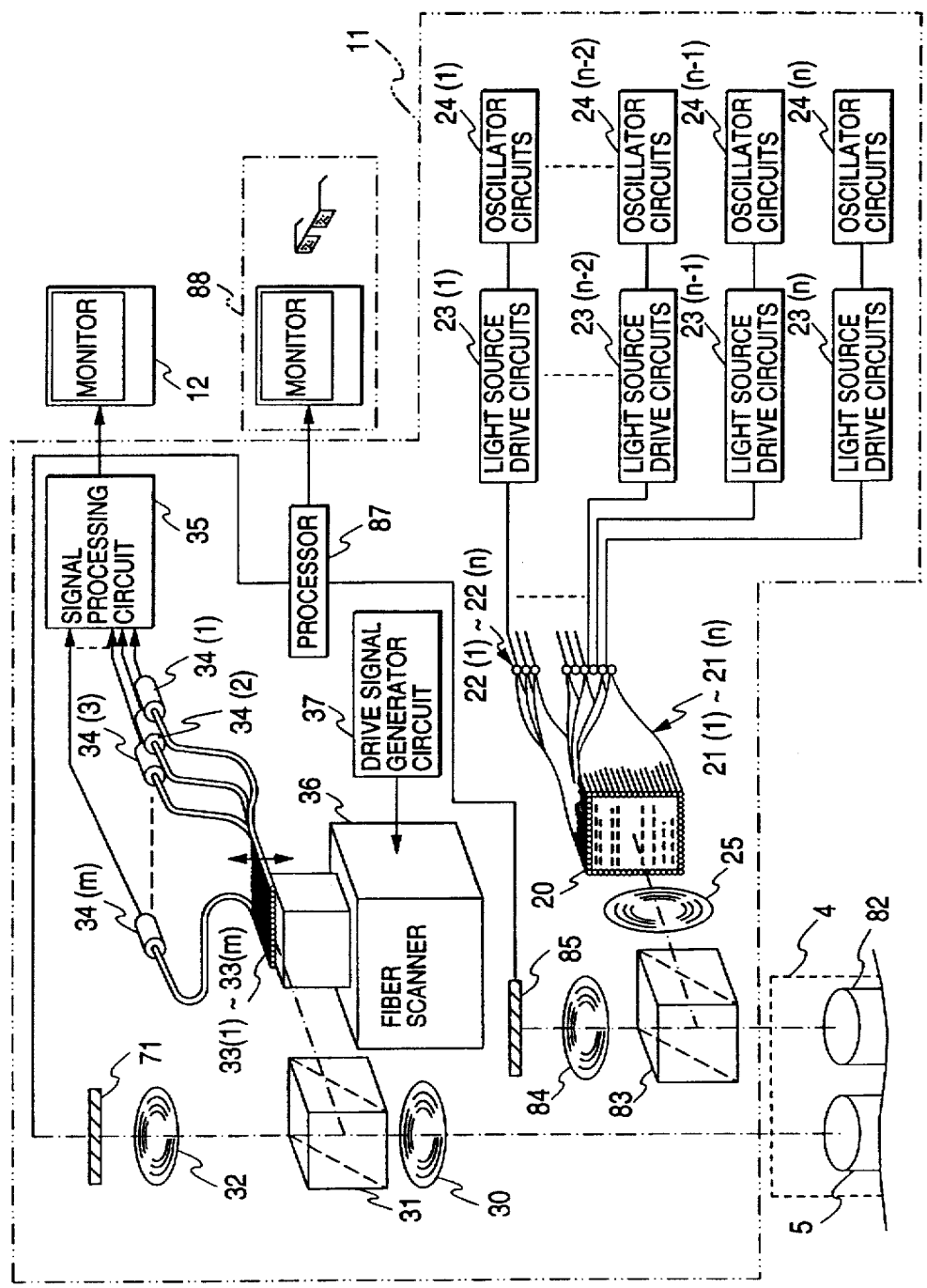
FIG. 19 shows the composition of the measuring head shown in FIG. 18.

We next describe the fifth embodiment of the invention with particular reference to FIGS. 18 and 19, in which FIG. 18 shows the construction of an endoscope apparatus for measuring three-dimensional configurations according to the fifth embodiment and FIG. 19 shows the composition of the measuring head shown in FIG. 18.

The fifth embodiment is essentially the same as the fourth embodiment, so the following description concerns only the differences between the two embodiments and the components which are common to both embodiments are identified by like numerals and will not be described in detail.

As shown in FIG. 18, the fifth embodiment differs from the fourth embodiment in that the measuring light projecting lens 14 and the measuring light transmitting image guide fiber 9 in the fourth embodiment are used as a second object imaging lens 81 and a second object image transmitting image guide 82 such that the first and second object imaging lenses 15 and 81 combine with the first and second object image transmitting image guides 5 and 82 to produce two images, which are combined by means of a stereoscopic display device to enable the viewing of a stereoscopic image.

As shown in FIG. 19, the means for generating the measuring light is provided not within the light source unit 10 but within the measuring head 11. In the measuring head 11, the measuring light focused by the imaging lens 25 is passed through a second beam splitter 83 to be launched into an end face of the second object image transmitting image guide 82; the measuring light transmitted through the second image guide 82 is focused by the second object imaging lens 81 to form an image on the object while, at the same time, the image of the object itself is focused at the end face of the second image guide 82. The focused object image is transmitted through the second image guide 82 in opposite direction, passed through the second beam splitter 83 and processed by an imaging lens 84 to be focused at a second imaging device 85. On the other hand, the image of the object that has passed through the imaging lens 30 for focusing at the measuring light's position detecting fibers 33(1) to 33(m) is passed through the beam splitter 31 and the auxiliary lens 32 to be focused at the first imaging device 71.

The outputs of the first and second imaging devices 71 and 85 are converted to respective image signals by a processor 87 and displayed on a stereoscopic display unit 88.

The other structural and operational features of the fifth embodiment are identical to the fourth embodiment. In the fifth embodiment, the advantages of the fourth embodiment are of course attained and, what is more, distance measurement can be accomplished with the added advantage of providing ease in viewing since the image of 2-D representation is transformed to a display having a stereoscopic effect.

Figure 20:
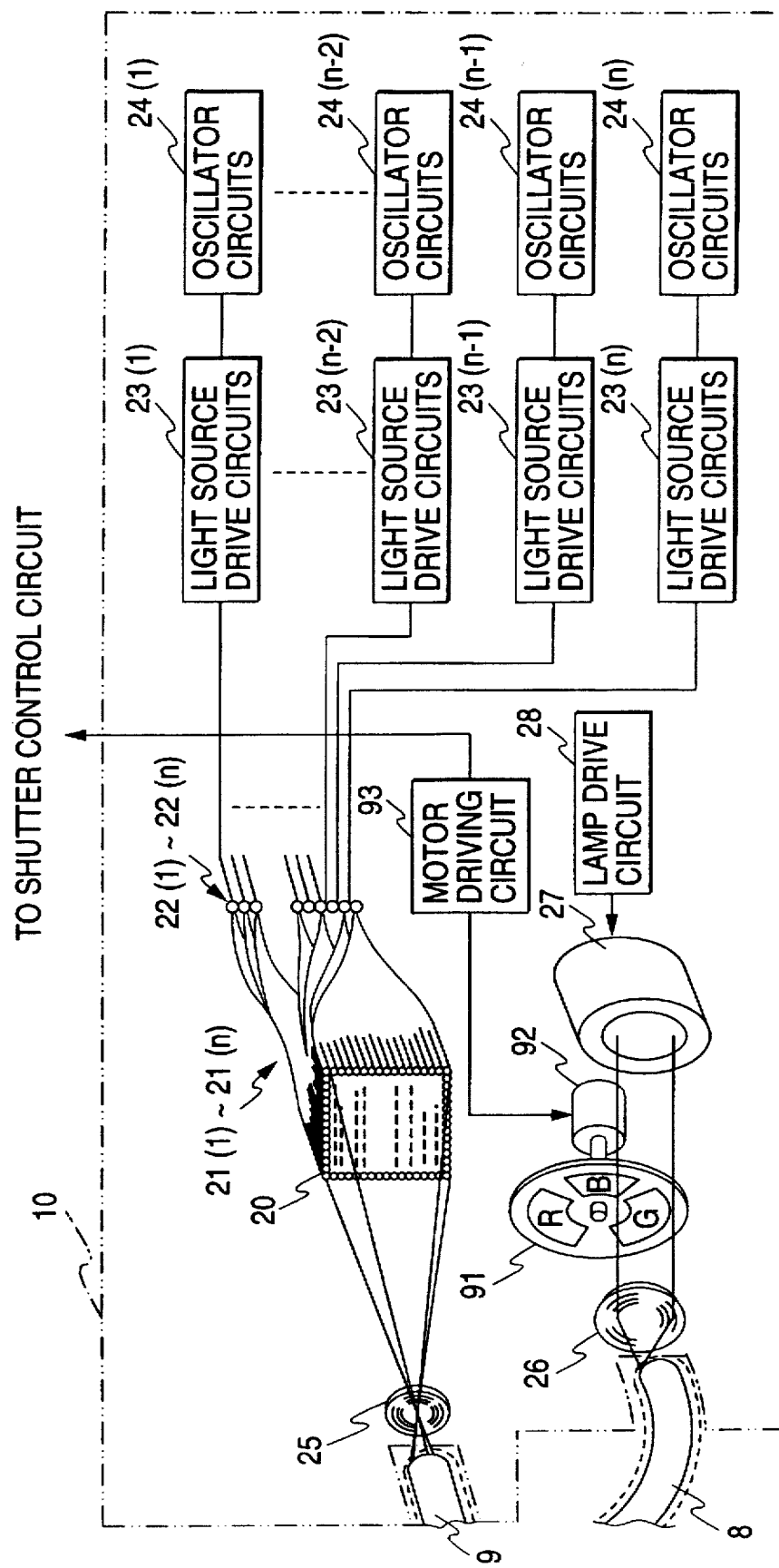
FIG. 20 shows the construction of the light source unit in an endoscope apparatus for measuring three-dimensional configuration according to a sixth embodiment of the invention.
Figure 21:
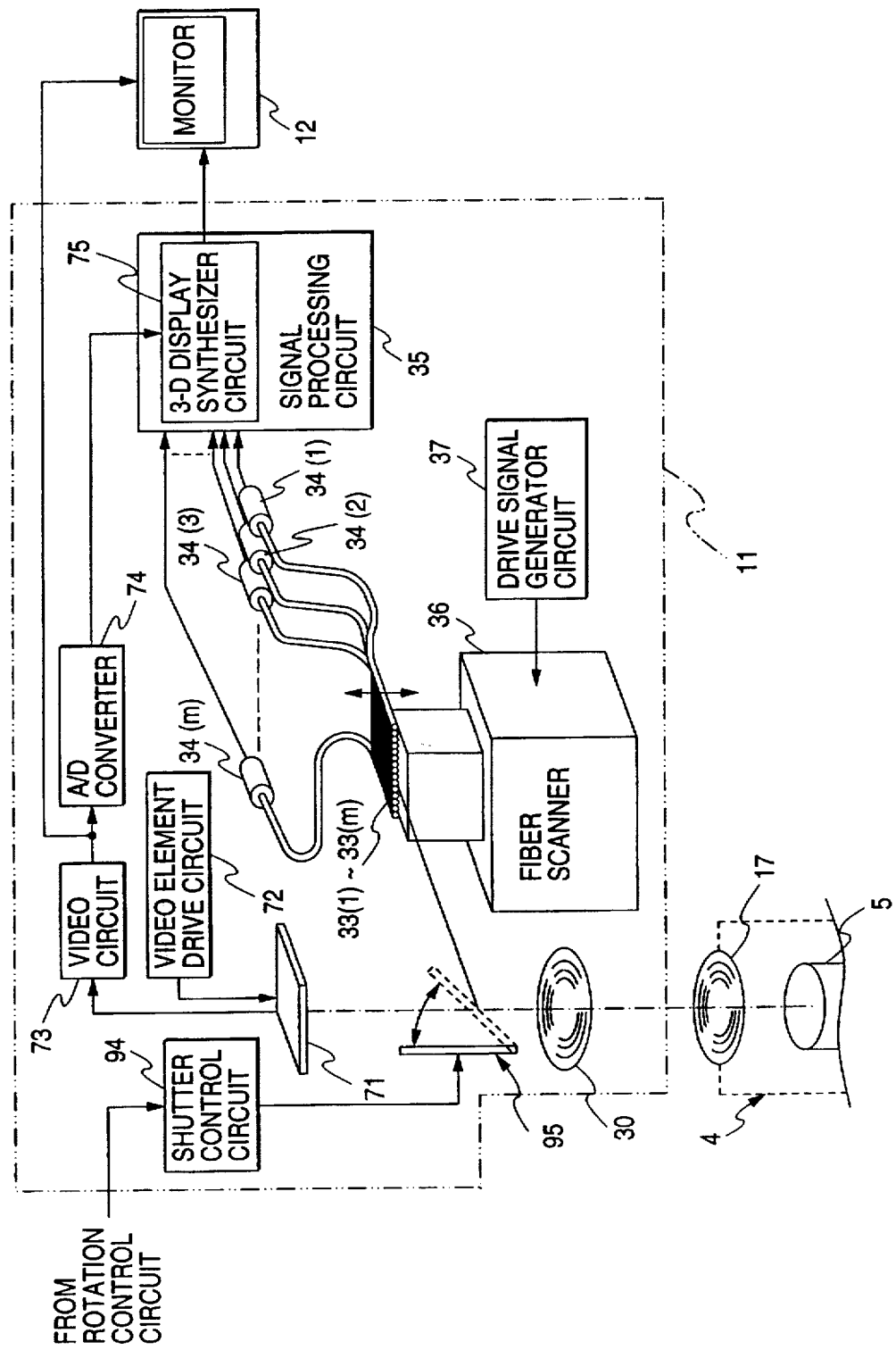
FIG. 21 shows the composition of a measuring head which performs measurement with the light supplied from the light source unit shown in FIG. 20.

We now describe the sixth embodiment of the invention with reference to FIGS. 20 and 21, in which FIG. 20 shows the construction of the light source unit in an endoscope apparatus for measuring three-dimensional configurations according to the sixth embodiment and FIG. 21 shows the composition of a measuring head which performs measurement with the light supplied from the light source unit shown in FIG. 20.

The sixth embodiment is essentially the same as the fourth embodiment, so the following description concerns only the differences between the two embodiments and the components which are common to both embodiments are identified by like numerals and will not be described in detail.

As shown in FIG. 20, the light source unit according to the sixth embodiment is modified as a frame sequential light source unit 10a which is commonly used with endoscopes and it includes a rotating filter 91 for successive application of R, G and B light, a servo motor 92 for driving the filter 91 to rotate, and a circuit 93 for controlling the rotation of servo motor 92. To implement this modification, the measuring head 11 is additionally equipped with a shutter control circuit 94 that is controlled with a shutter control signal from the rotation control circuit 93 and the beam splitter 31 in the fourth embodiment is replaced by a shutter 95 which is controllable with the shutter control circuit 94.

The other structural aspects of the sixth embodiment are identical to the fourth embodiment.

As with conventional frame sequential electronic endoscopes, the servo motor 92 is controlled by the rotation control circuit 93 and the rotating filter 91 coupled to the circuit 92 is rotated to apply R, G and B components of light sequentially onto the object, which components are received by the imaging device 71 and signals for the R, G and B components are individually stored in an image memory (not shown) such that they are synthesized into a single frame, from which a 2-D endoscopic image is constructed.

If the filter 91 has rotated to such a position that the R, G and B components of light are blocked rather than transmitted, the rotation control circuit 93 will transmit the relevant information to the shutter control circuit 94; in response to this information, the circuit 94 will move the shutter 95 in such a direction that it will block the optical path to the imaging device 71 while admitting the optical path to the measuring light's position detecting fibers 33(1) to 33(m). The shutter 95 shown in FIG. 21 is of a mirror type for switching between optical paths; if desired, it may be of such a type that either one of two optical paths is blocked by a driven liquid crystal.

The other operational features of the sixth embodiment are the same as in the fourth embodiment. In the sixth embodiment, the advantages of the fourth embodiment are of course attained and, in addition, there is no likelihood for the 3-D measuring light to cause adverse effects on the color reproduction of ordinary endoscopic images.

Figure 22:
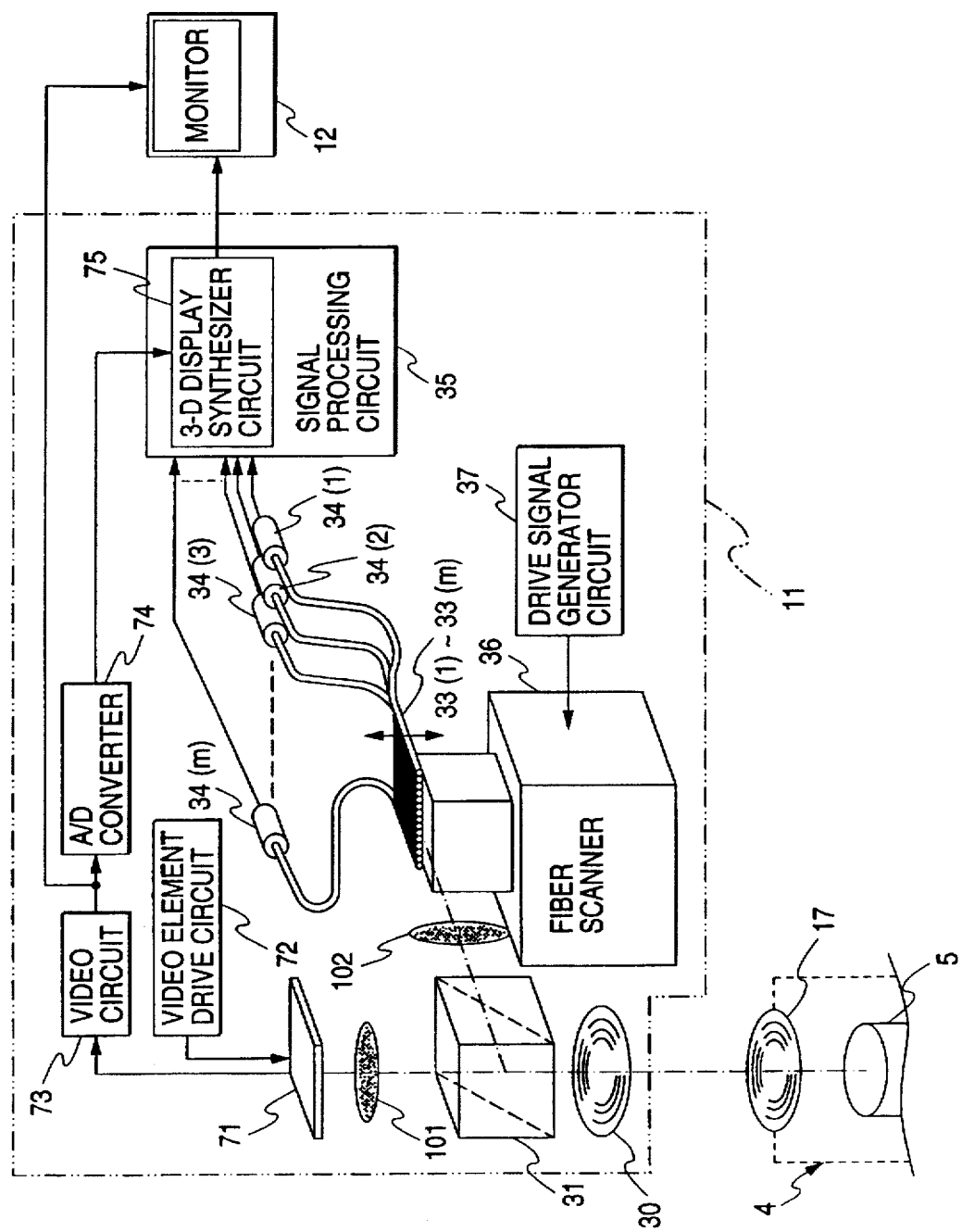
FIG. 22 shows the composition of a measuring head according to a seventh embodiment of the invention.

We next describe the seventh embodiment of the invention with particular reference to FIG. 22 which shows the composition of a measuring head according to the seventh embodiment.

The seventh embodiment is essentially the same as the fourth embodiment, so the following description concerns only the differences between the two embodiments and the components which are common to both embodiments are identified by like numerals and will not be described in detail.

As shown in FIG. 22, the measuring head indicated by 11 has a visible light transmissive filter 101 and an infrared light transmissive filter 102; the filter 101 is provided in front of the imaging device 71 for transmitting only light in the visible range whereas the filter 102 is provided in front of the measuring light's position detecting fibers 33(1) to 33(m) for transmitting only light in the infrared range. This arrangement is adopted when an irradiation is used as the measuring light and, hence, their light source may be replaced by the combination of another invisible light source and a filter.

The other structural and operational features of the seventh embodiment are identical to those of the fourth embodiment. In the seventh embodiment, the advantages of the fourth embodiment are of course attained and, in addition, the precision in measurement is improved by eliminating extraneous light that would otherwise interfere with the 2-D or 3-D image (i.e., crosstalk between the 2-D and 3-D images is effectively eliminated).

Figure 23:
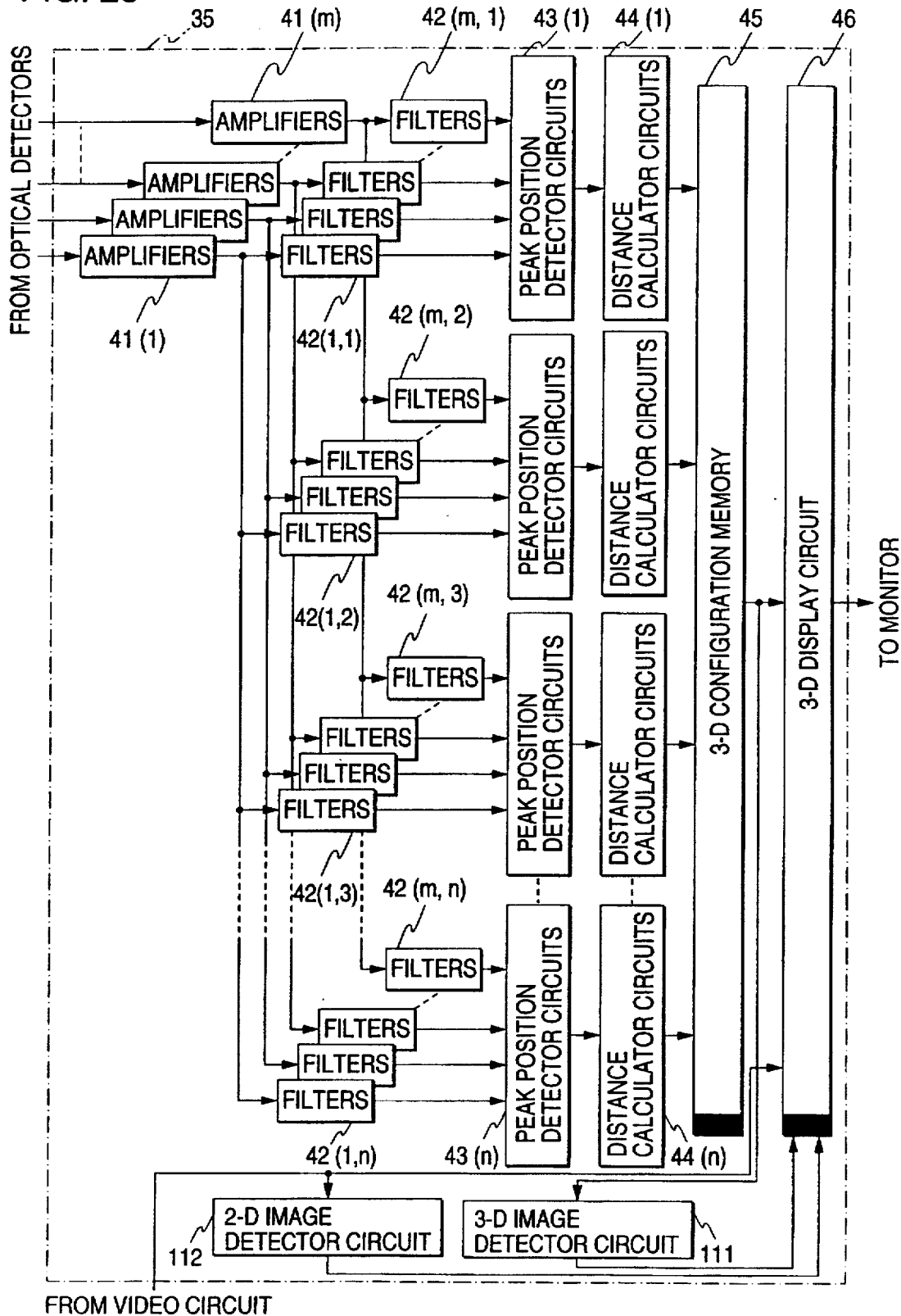
FIG. 23 shows the configuration of a signal processing circuit in a measuring head according to an eighth embodiment of the invention.

We next describe the eighth embodiment of the invention with particular reference to FIG. 23 which shows the configuration of a signal processing circuit in a measuring head according to the eighth embodiment.

The eighth embodiment is essentially the same as the fourth embodiment, so the following description concerns only the differences between the two embodiments and the components which are common to both embodiments are identified by like numerals and will not be described in detail.

As shown in FIG. 23, the signal processing circuit 35 in the measuring head of the eighth embodiment has a 3-D image detector circuit 111 and a 2-D image detector circuit 112. These detectors sense any abnormalities in the respective image signals and the results of detection are sent to the 3-D display synthesizer circuit 75.

The 3-D display synthesizer circuit 75 performs such a control that if any abnormality is found in the image that is being viewed on the monitor 12 by means of a 2-D or 3-D image signal, the circuit will automatically select the other image (3-D image if the 2-D image is abnormal and vice versa) and output it to the monitor.

The other structural and operational features of the eighth embodiment are identical to those of the fourth embodiment. In the eighth embodiment, the advantages of the fourth embodiment are of course attained and, in addition, greater safety is assured in the case of troubles and the like.

Figure 24:
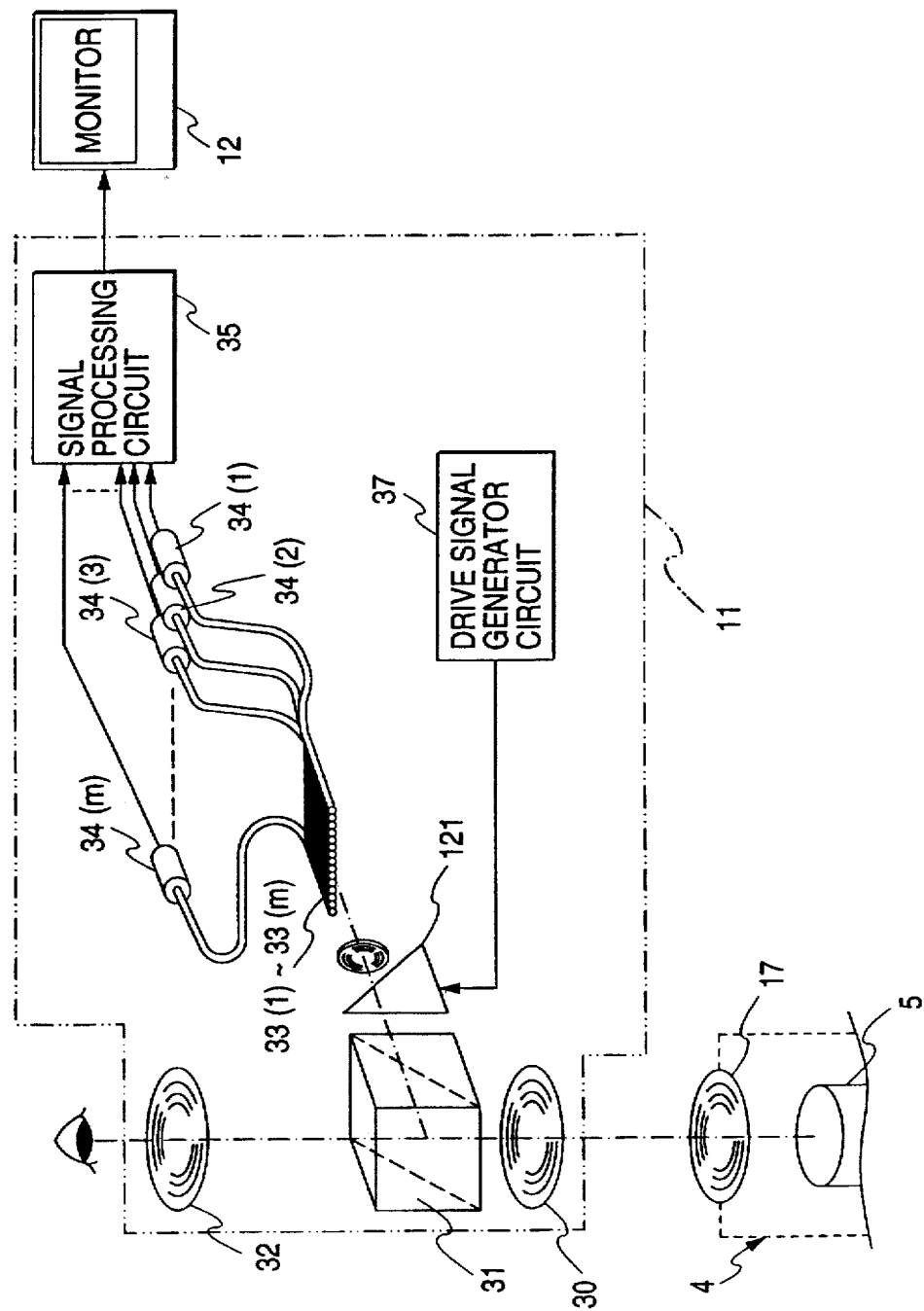
FIG. 24 shows the composition of a measuring head according to a ninth embodiment of the invention.

We next describe the ninth embodiment of the invention with reference to FIG. 24 which shows the composition of a measuring head according to the ninth embodiment.

The ninth embodiment is essentially the same as the first embodiment, so the following description concerns only the differences between the two embodiments and the components which are common to both embodiments are identified by like numerals and will not be described in detail.

As shown in FIG. 24, the ninth embodiment does not have the fiber scanner 36 used in the first embodiment but substitutes an electro-optical deflector 121 typically composed of a ferroelectric or liquid crystal.

The other structural aspects of the ninth embodiment are identical to the first embodiment.

A drive signal generated from the circuit 37 will change the refractive index of the electro-optical deflector 121 typically composed of a ferroelectric or liquid crystal. The resulting change in refractive index can be utilized to change the direction of light travel such as to scan the light traveling toward the measuring light's position detecting fibers 33(1) to 33(m).

The other operational features of the ninth embodiment are the same as in the first embodiment. Compared to the first embodiment, the ninth embodiment experiences less mechanical vibrations and hence claims a longer life and higher reliability.

Figure 25:
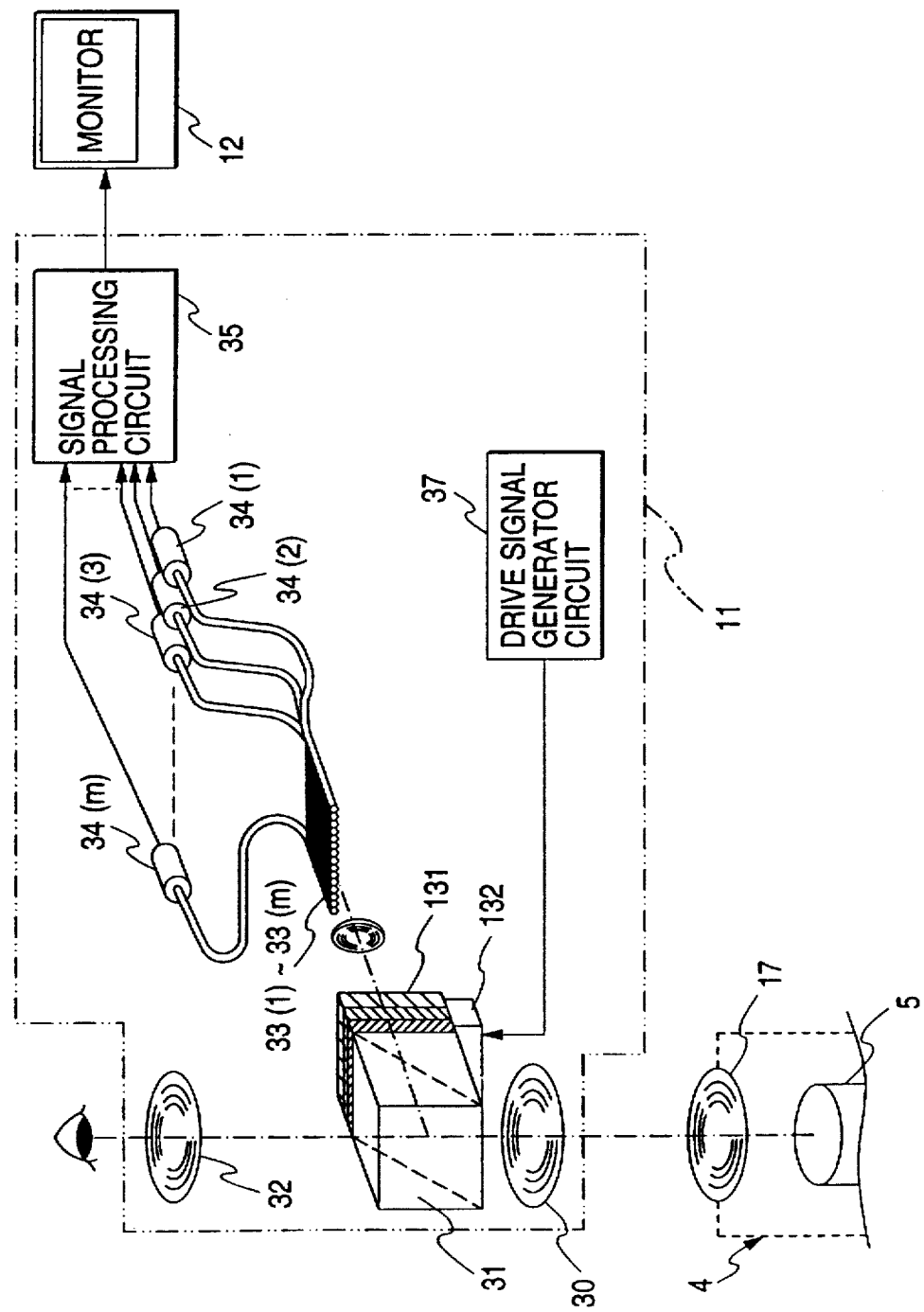
FIG. 25 shows the composition of a measuring head according to a tenth embodiment of the invention.

We now describe the tenth embodiment of the invention with particular reference to FIG. 25 which shows the composition of a measuring head according to the tenth embodiment.

The tenth embodiment is essentially the same as the first embodiment, so the following description concerns only the differences between the two embodiments and the components which are common to both embodiments are identified by like numeral and will not be described in detail.

As shown in FIG. 25, the tenth embodiment does not have the fiber scanner 36 used in the first invention but substitutes a transparent medium 131 and a heater 132.

The other structural aspects of the tenth embodiment are identical to the first embodiment.

A drive signal generated from the circuit 37 will actuate the heater 132 which then generates heat. The generated heat will change the refractive index profile within the transparent medium 131 and the resulting change in the index profile can be utilized to change the direction of light travel such as to scan the light traveling toward the measuring light's position detecting fibers 33(1) to 33(m).

The other operational features of the tenth embodiment are identical to the first embodiment. As in the ninth embodiment, mechanical vibrations are less likely to occur in the tenth embodiment than in the first embodiment and, hence, a longer life and higher reliability can be achieved.

Figure 26:
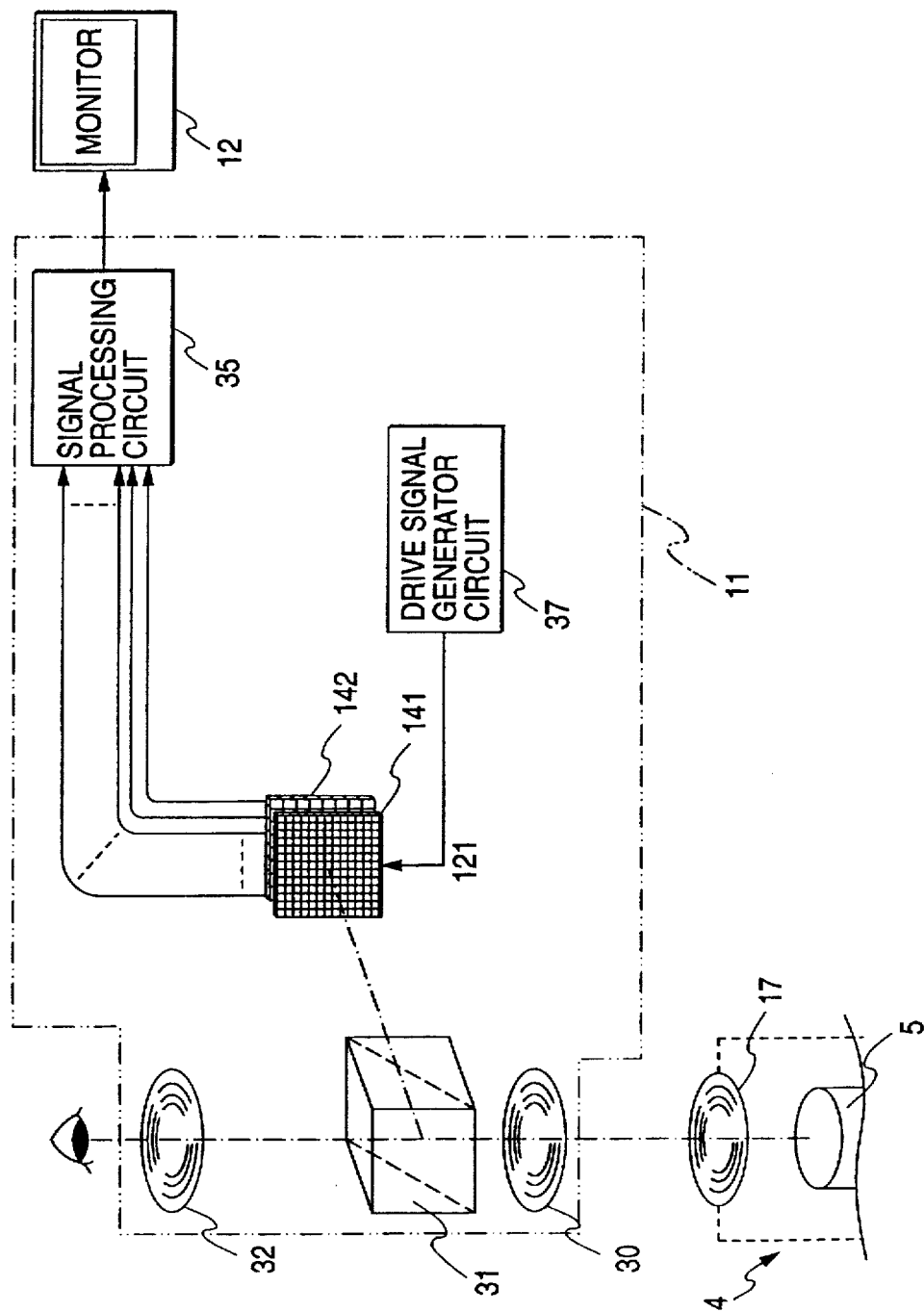
FIG. 26 shows the composition of a measuring head according to an eleventh embodiment of the invention.

We next describe the eleventh embodiment of the invention with reference to FIG. 26 which shows the composition of a measuring head according to the eleventh embodiment.

The eleventh embodiment is essentially the same as the first embodiment, so the following description concerns only the differences between the two embodiments and the components which are common to both embodiments are identified by like numerals and will not be described in detail.

As shown in FIG. 26, the eleventh embodiment does not have the measuring light's position detecting fibers 33(1) to 33(m) or the fiber scanner 36 which are used in the first embodiment but substitutes a spatial optical modulator 141 and a photodiode array 142. In response to a drive signal generated from the circuit 37, the spatial optical modulator 141 is rendered transmissive of light (as in the case of a liquid crystal that is turned on or off) for successive horizontal lines; therefore, the photodiode array 142 provided behind the modulator 141 is so adapted that it receives only light in one horizontal line.

The other structural aspects of the eleventh embodiment are identical to the first embodiment.

The light emerging the exit end of the object image transmitting image guide 5 is focused on the spatial optical modulator 141 and the photodiode array 142 positioned on and in intimate contact with the modulator 141 (or combined with a lens such that it is optically conjugated with the modulator 141) is adapted to receive the light that has passed through the modulator 141.

By ensuring that in response to the drive signal generated from the circuit 37, the spatial optical modulator 141 is turned on (rendered transmissive of light) for successive horizontal lines, one can obtain signals that are similar to those produced in the first embodiment by vibrating the measuring light's position detecting fibers 33(1) to 33(m).

The other operational features of the eleventh embodiment are identical to the first embodiment. As in the ninth embodiment, mechanical vibrations are less likely to occur in the eleventh embodiment than in the first embodiment and, hence, a longer life and higher reliability can be achieved.

Figure 27:
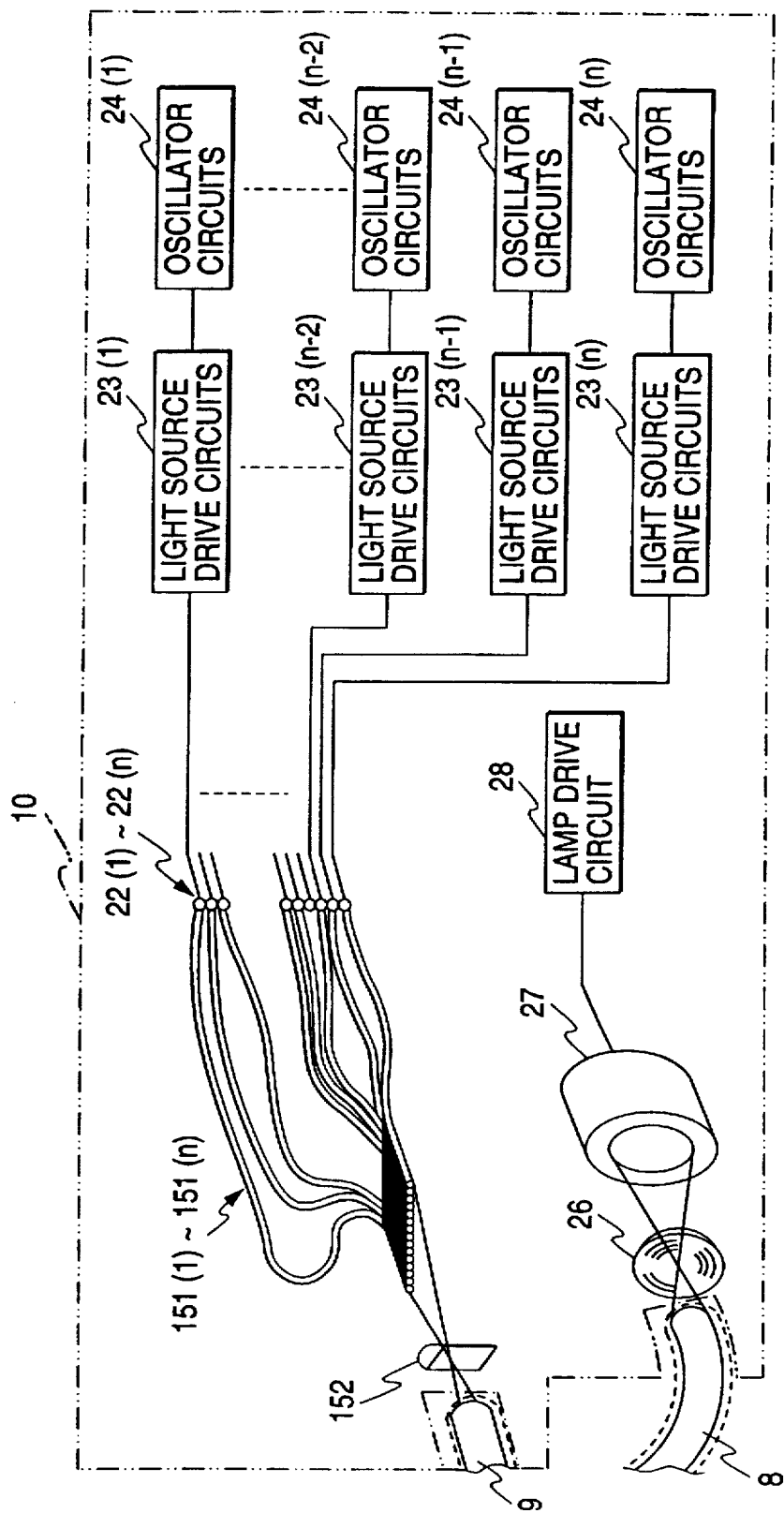
FIG. 27 shows the composition of a light source unit according to a twelfth embodiment of the invention.

We next describe the twelfth embodiment of the invention with reference to FIG. 27 which shows the composition of a light source unit according to the twelfth embodiment.

The twelfth embodiment is essentially the same as the first embodiment, so the following description concerns only the differences between the two embodiments and the components which are common to both embodiments are identified by like numerals and will not be described in detail.

As shown in FIG. 27, the optical fiber bundles 21(1) to 21(n) in the light source unit 10 according to the first embodiment are modified in the twelfth embodiment in such a way that discrete optical fibers 151(1) to 151(n) are coupled at an end to n light sources and aligned in a row at the other end. Provided ahead of the aligned ends of the fibers is imaging optics using a cylindrical lens 152.

The other structural aspects of the twelfth embodiment are identical to the first embodiment.

Light issuing from the n light sources is launched into the individually separate optical fibers 151(1) to 151(n) and emerge from their end faces aligned in a row. The imaging optics using the cylindrical lens 152 is capable of projecting a single point as a straight line, so the light issuing from each of the fibers 151(1) to 151(n) is projected as a straight line at the entrance end of the measuring light transmitting fiber 9. The fibers 151(1) to 151(n) are n in number, so as in the case of the first embodiment, n lines of line-shaped light will eventually be projected at the entrance end of the light measuring transmitting fiber 9.

The other operational features of the twelfth embodiment are the same as in the first embodiment. Therefore, the advantages of the first embodiment are assured even if the number of optical fiber bundles is reduced to one and the fibers in one bundle are separated individually.

If desired, the optical fibers 151(1) to 151(n) may be replaced by n light sources aligned in a row. The imaging optics may be composed of an anamorphic lens or EOD (electro-optical deflector) in place of the cylindrical lens.

Figure 28:
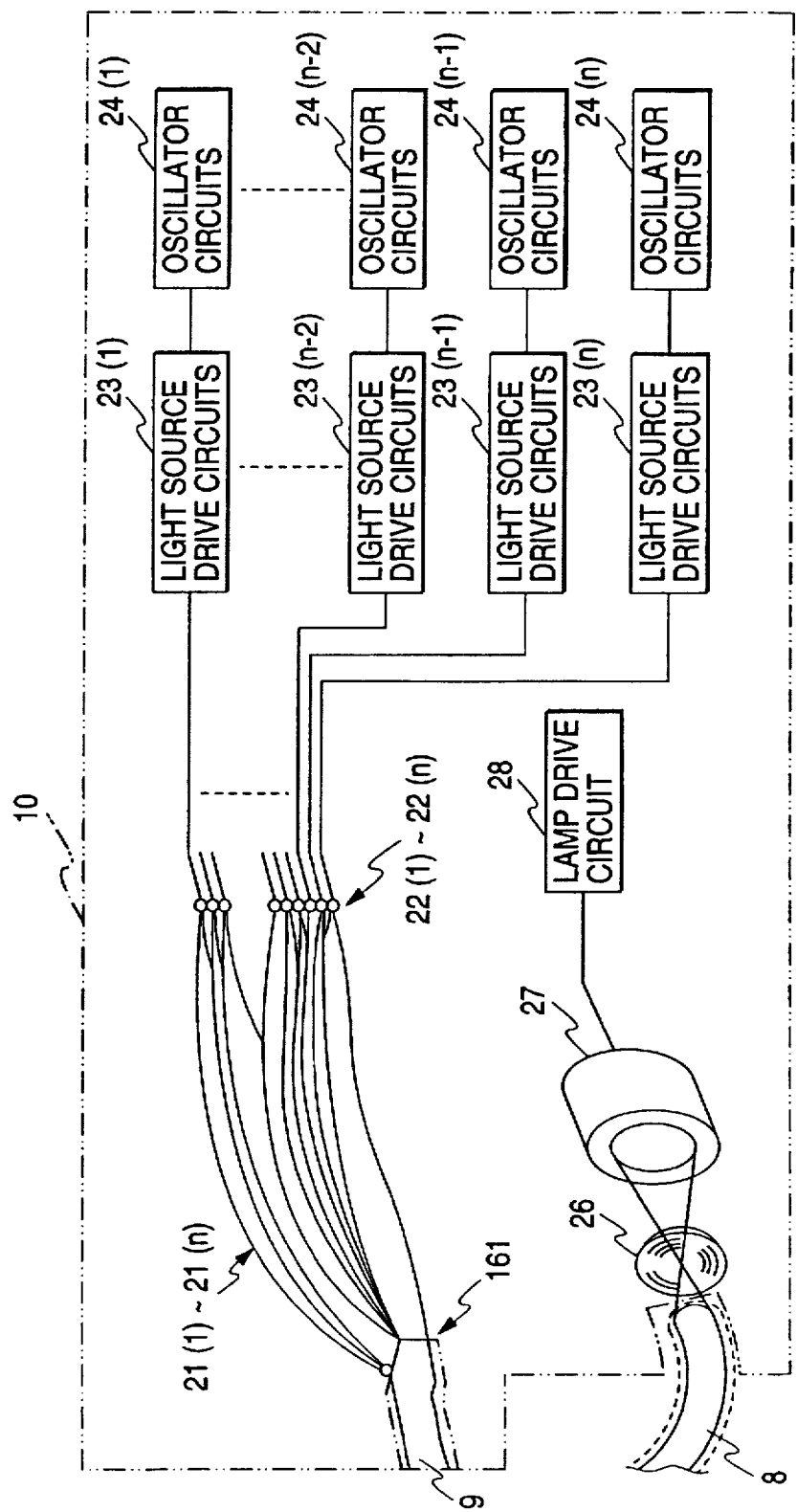
FIG. 28 shows the composition of a light source unit according to a thirteenth embodiment of the invention.
Figure 29:
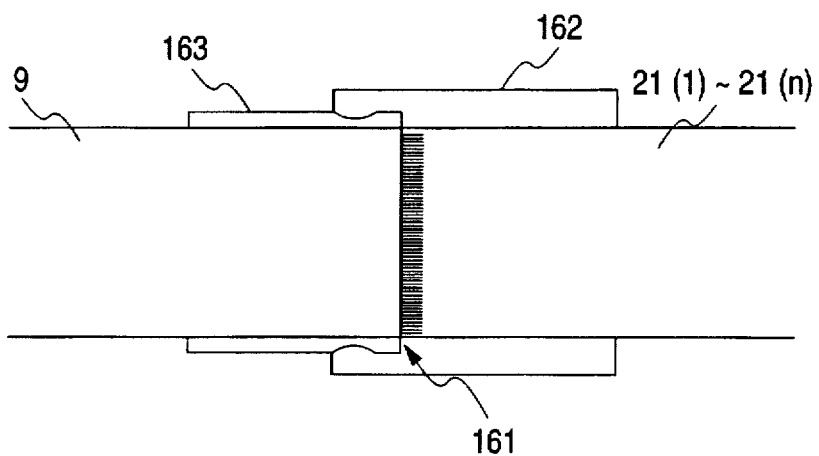
FIG. 29 shows in detail the connection between the exit end face of each of the optical fiber bundles shown in FIG. 28 and the measuring light transmitting image guide fiber also shown in FIG. 28.

We now describe the thirteenth embodiment of the invention with reference to FIGS. 28 and 29, in which FIG. 28 shows the composition of a light source unit according to the thirteenth embodiment and FIG. 29 shows in detail the connection between the exit end face of each of the optical fiber bundles shown in FIG. 28 and the measuring light transmitting image guide fiber also shown in FIG. 28.

The thirteenth embodiment is essentially the same as the first embodiment, so the following description concerns only the differences between the two embodiments and the components which are common to both embodiments are identified by like numerals and will not be described in detail.

As shown in FIG. 28, the thirteenth embodiment which is a modified version of the light source unit 10 in the first embodiment does not use the imaging lens 25 but has the exit end face of each of the optical fiber bundles 21(1) to 21(n) connected to the measuring light transmitting image guide fiber 9 by means of a connection 161. Since the imaging lens 25 is not used, the thirteenth embodiment is superior to the first embodiment in that it prevents the optical loss (reduces light quantity) which would otherwise occur if the imaging lens 25 were used.

The connection between the exit end face of each of the optical fiber bundles 21(1) to 21(n) and the measuring light transmitting image guide fiber 9 is shown enlarged in FIG. 29. The fiber bundles 21(1) to 21(n) are gathered and worked to have an exit end face having the same external shape as the entrance and face of the measuring light transmitting image guide fiber 9. As also shown in FIG. 29, the connection 161 includes a first connector 162 and a second connector 163 for ensuring that the fiber bundles and the guide fiber are fixed in position to have intimate contact with each other.

The other structural and operational features of the thirteenth embodiment are the same as in the first embodiment. Since the exit end face of each of the optical fiber bundles 21(1) to 21(n) is in intimate contact with the entrance end face of the measuring light transmitting image guide fiber 9, the light issuing from the fiber bundles is transmitted as such through the guide fiber 9. Functionally, this is equivalent to the first embodiment in which n lines of line-shaped light are focused at the entrance face of the measuring light transmitting image guide fiber 9.

Figure 30:
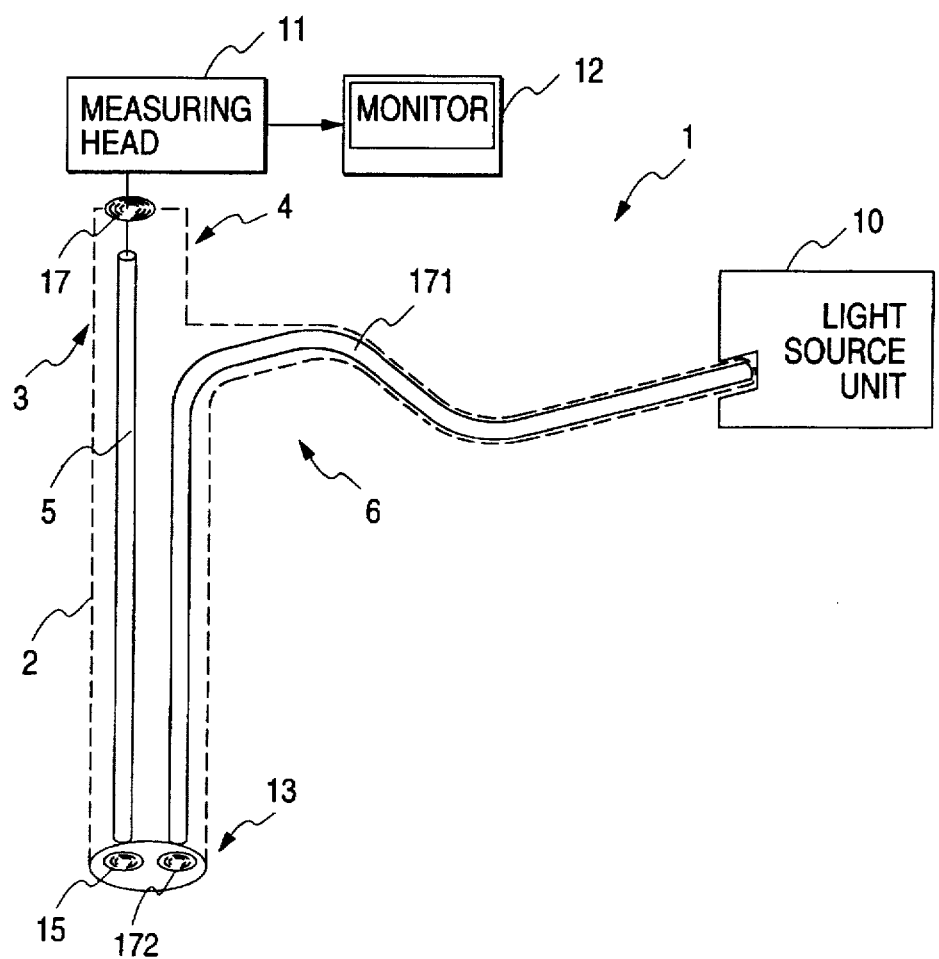
FIG. 30 shows the construction of an endoscope apparatus for measuring three-dimensional configurations according to a fourteenth embodiment of the invention.
Figure 31:
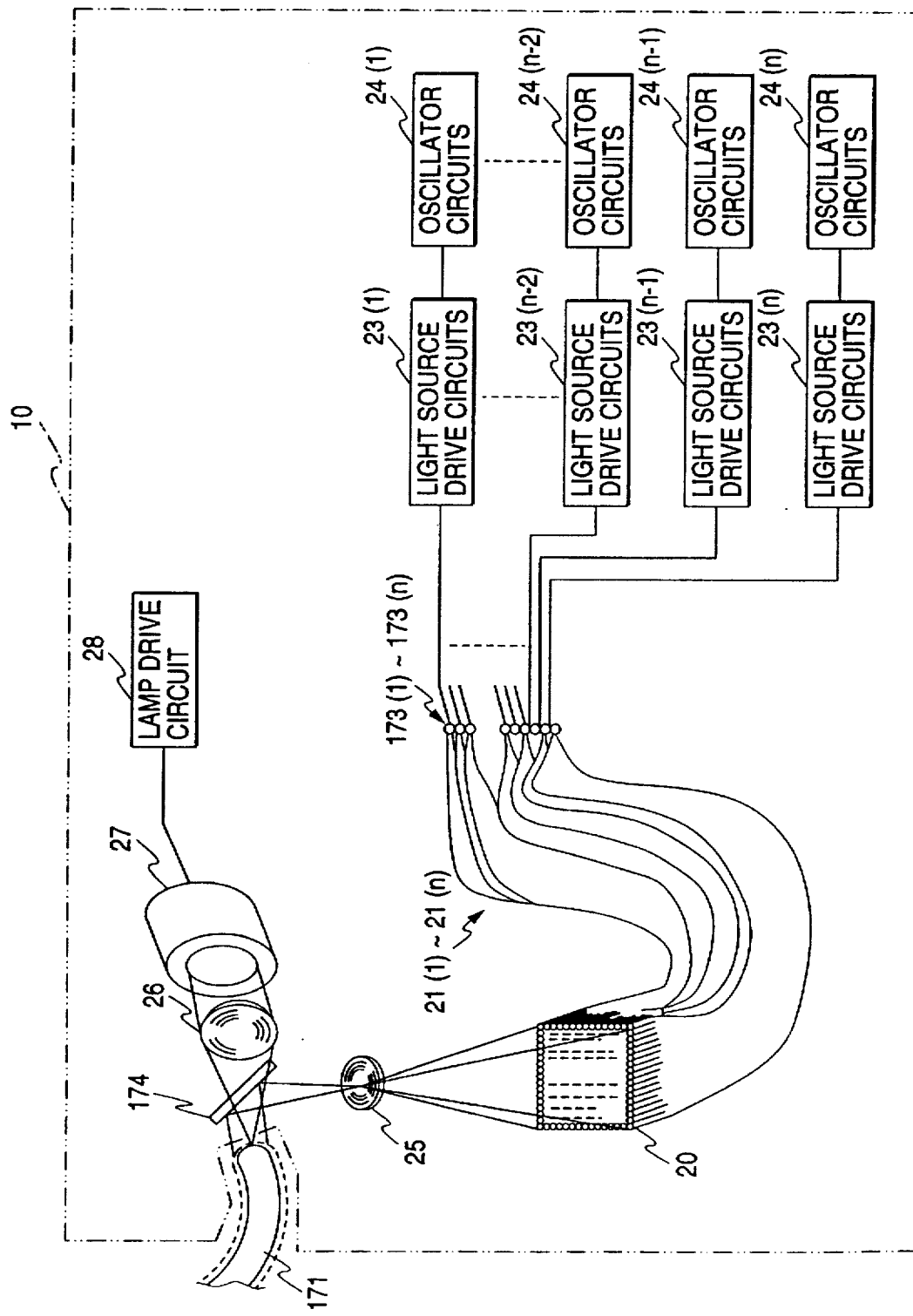
FIG. 31 shows the composition of the light source unit shown in FIG. 30.
Figure 32:
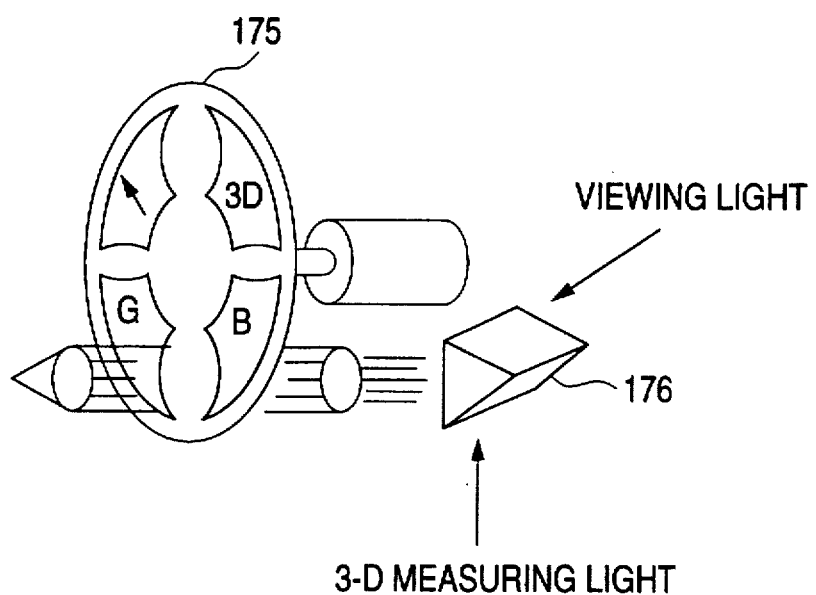
FIG. 32 shows the layout of a 3-D/2-D rotating filter and prism combination that can be substituted for the infrared reflecting mirror shown in FIG. 31.

We now describe the fourteenth embodiment of the invention with reference to FIGS. 30 to 32, in which: FIG. 30 shows the construction of an endoscope apparatus for measuring three-dimensional configurations according to the fourteenth embodiment; FIG. 31 shows the composition of the light source unit shown in FIG. 30; and FIG. 32 shows the layout of a 3-D2-D rotating filter and prism combination that can be substituted for the infrared reflecting mirror shown in FIG. 31.

The fourteenth embodiment is essentially the same as the first embodiment, so the following description concerns only the differences between the two embodiments and the components which are common to both embodiments are identified by like numerals and will not be described in detail.

As shown in FIG. 30, the fourteenth embodiment differs from the first embodiment in that the functions of both the lightguide 8 and the measuring light transmitting image guide fiber 9 are fulfilled simultaneously by a single image guide fiber 171. Indicated by 172 in FIG. 30 is a lens that serves to project the measuring light and illuminate the object (for the purpose of the present discussion, this lens is hereunder referred to simply as a "projection lens"). If a conventional endoscopic objective lens is used as the projection lens, not only the measuring light but also the illuminating light will be focused at the object. In other words, the structure of the exit end face of the image guide fiber 171 (which consists of the light core portion and the dark cladding portion) will be projected onto the object.

To avoid this problem, the light source unit 10 employs infrared sources 173(1) to 173(n) as the sources of the measuring light (see FIG. 31) and the projection lens 172 is designed as optics having a different focal length at the wavelength of the measuring light than at the wavelength of the visible light (illuminating light). This lens optics need be adapted to permit aberrational correction at the wavelength of the measuring light but it may be either over-or undercorrected in the visible range. This ensures that the structure of the exit end face of the image guide fiber 171 will not be imaged at the object under the illuminating light but imaged under the measuring light.

At the entrance end of the image guide fiber 171, an infrared reflecting mirror 174 which reflects only their radiation (at the wavelength of the measuring light) is provided to insure that the illuminating light and the measuring light will simultaneously be launched into the guide fiber 171. In this way, the infrared component of the illuminating light will not be admitted into the fiber, thereby ensuring against the "thermal scorch" of the entrance face of the fiber and yet the measuring light can effectively be admitted into the fiber.

The other structural and operational features of the fourteenth embodiment are identical to the first embodiment. In addition to the advantages obtained in the first embodiment, the insertable portion 11 of an endoscope can be reduced in diameter by a sufficient degree to relieve the discomfort to the patient.

If desired, the concept of the fourteenth embodiment may be applied to a frame sequential electronic endoscope and to this end, their reflecting mirror 174 is replaced by the combination of a 3-D/2-D rotating filter 175 and a prism 176 (see FIG. 32) such that the rotation of the filter, the emission of the measuring light, the driving of the imaging device and the video processing are performed in an appropriately timed relationship, thereby allowing the viewing light and the measuring light to be issued alternately.

Figure 33:
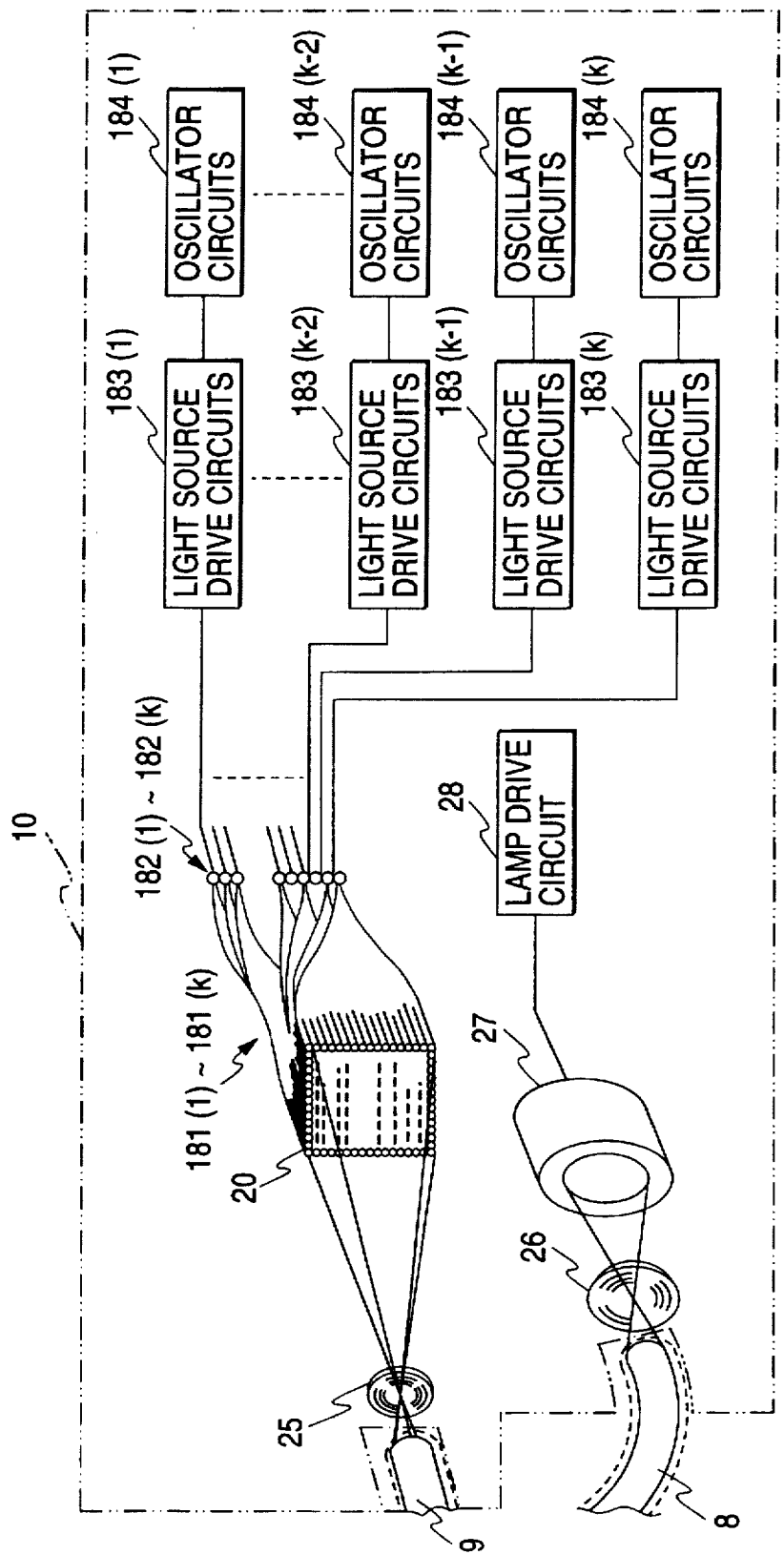
FIG. 33 shows the composition of a light source unit according to a fifteenth embodiment of the invention.
Figure 34:
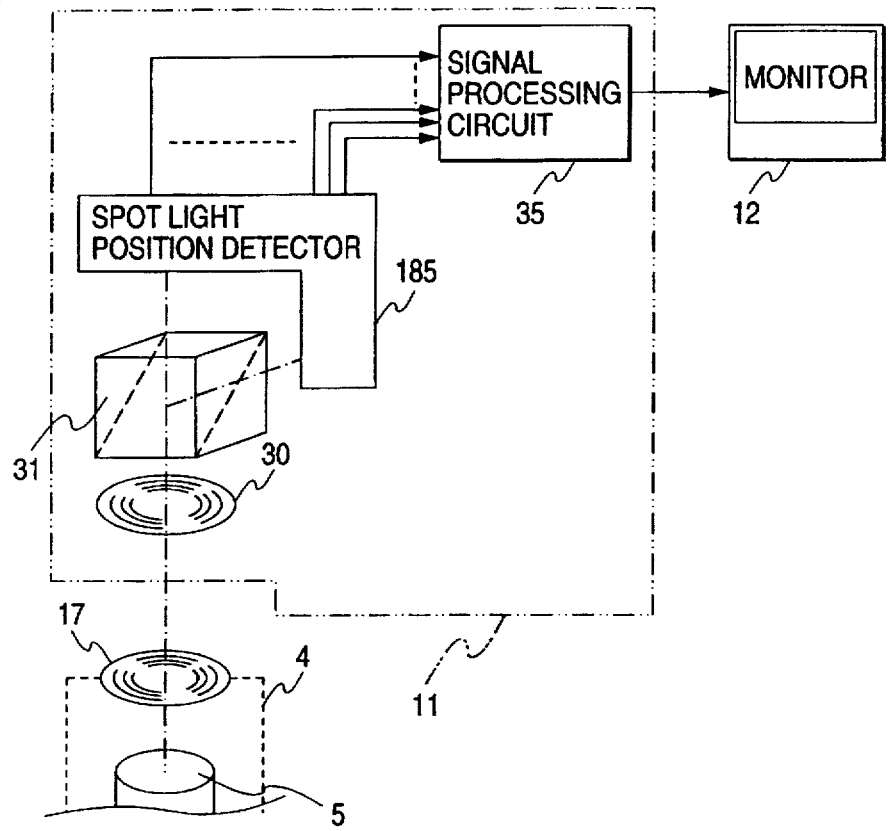
FIG. 34 shows the composition of a measuring head which performs measurement with the measuring light from the light source unit shown in FIG. 33.
Figure 35:
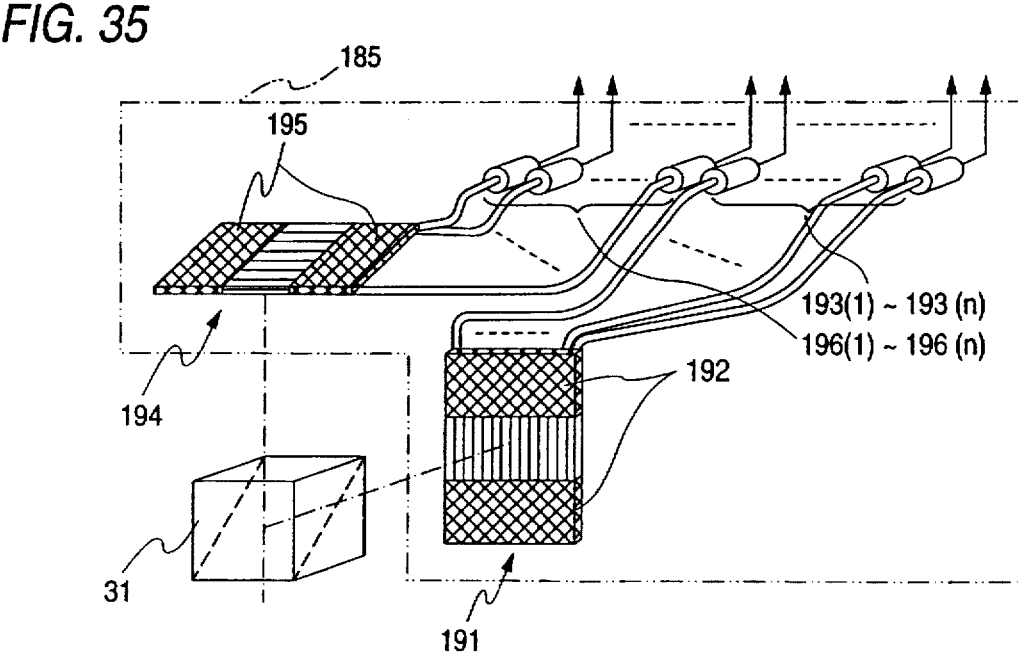
FIG. 35 shows the composition of the spot light position-sensitive detector shown in FIG. 34.

We next describe the fifteenth embodiment of the invention with reference to FIGS. 33 to 35, in which: FIG. 33 shows the composition of a light source unit according to the fifteenth embodiment; FIG. 34 shows the composition of a measuring head which performs measurement with the measuring light from the light source unit shown in FIG. 33; and FIG. 35 shows the composition of the spot light position detector shown in FIG. 34.

The fifteenth embodiment is essentially the same as the first embodiment, so the following description concerns only the differences between the two embodiments and the components which are common to both embodiments are identified by like numerals and will not be described in detail.

In the first embodiment, n optical fiber bundles are used to generate n lines of line-shaped light for measurement whereas in the fifteenth embodiment, k optical fibers are used to generate k spots of light for the same purpose.

As shown in FIG. 33, the light source unit 10 in the fifteenth embodiment has optical fibers 181(1) to 181(k), light sources 182(1) to 182(k), drive circuits 183(1) to 183(k) and oscillator circuits 184(1) to 184(k).

As shown in FIG. 34, the measuring head 11 has a spot light position detector 185 provided as means for generating spot light having a plurality of frequency components. As shown specifically in FIG. 35, the spot light position detector 185 comprises horizontal (H) position detecting fibers 191(1) to 191(n), light shielding means 192 and H optical detectors 193(1) to 193(n), as well as vertical (V) position detecting fibers 194(1) to 194(n), light shielding means 195 and H optical detectors 196(1) to 196(n). The H position detecting fibers 191(1) to 191(n) are positioned to cross with the V position detecting fibers 194(1) to 194(n) at right angles.

The other structural aspects of the fifteenth embodiment are identical to the first embodiment.

The procedure for generating a plurality of light spots is identical to the procedure for generating more than one line-shaped light in the first embodiment, except that a single fiber rather than a fiber bundle is used to generate a light spot. Needless to say, the optical fibers 181(1) to 181(k), light sources 182(1) to 182(k), drive circuits 183(1) to 183(k) and oscillator circuits 184(1) to 184(k) have to be increased in number in order to perform measurement over the same area as in the first embodiment.

The spot light having a plurality of frequency components as projected from the measuring light projecting lens 14 is reflected by the object and is passed through the objective lens 15, the object image transmitting image guide 5 and other components to be admitted into the beam splitter 31, where it is split into two beamlets. One of the beamlets emerging from the beam splitter 31 is launched into the lateral side of each of the H position detecting fibers 191(1) to 191(n). Part of the incident light is reflected by fibers and part is transmitted through the lateral side of each fiber but part of the transmissive light propagates through each fiber to reach the exit end. The emerging light is detected by either one of the H optical detectors 193(1) to 193(n) provided at the exit end of the fibers and this enables identification of the fiber that received the incident spot light. The position of the fiber receiving the incident light is caused to deviate from the reference position by the surface state of the object and, hence, the distance in the horizontal direction can be calculated by checking the positional deviation against the lookup table in the distance calculating circuits 44(1) to 44(n).

Similarly, the other beamlet emerging from the beam splitter 31 is launched into the lateral side of each of the V position detecting fibers 194(1) to 194(n), enabling the calculation of distances in the vertical direction.

As in the first embodiment, the results obtained by these procedures are processed to separate the respective frequency components by means of filters $42(x,1)$ to $42(x,n)$ ($x=1, 2, \ldots, m$) and peak position detector circuits 43(1) to 43(n) and mathematical operations are repeated the necessary times in the distance calculating circuits 44(1) to 44(n) to generate data representing the three-dimensional configuration of the object.

In the fifteenth embodiments, light shield means 192 and 195 are provided to ensure that the optical fibers will not admit any light other than the spot light. Although not shown, light diffusing means may be provided between the beam splitter 31 and each of the optical fibers to reduce the component of light that is reflected from the lateral side of each fiber while permitting more light to be launched into each optical detector; this would reduce the gains of amplifiers 41(1) to 41(n) in a subsequent stage, thereby contributing to a smaller noise component.

The other operational and functional features of the fifteenth embodiment are the same as in the first embodiment.

Figure 36:
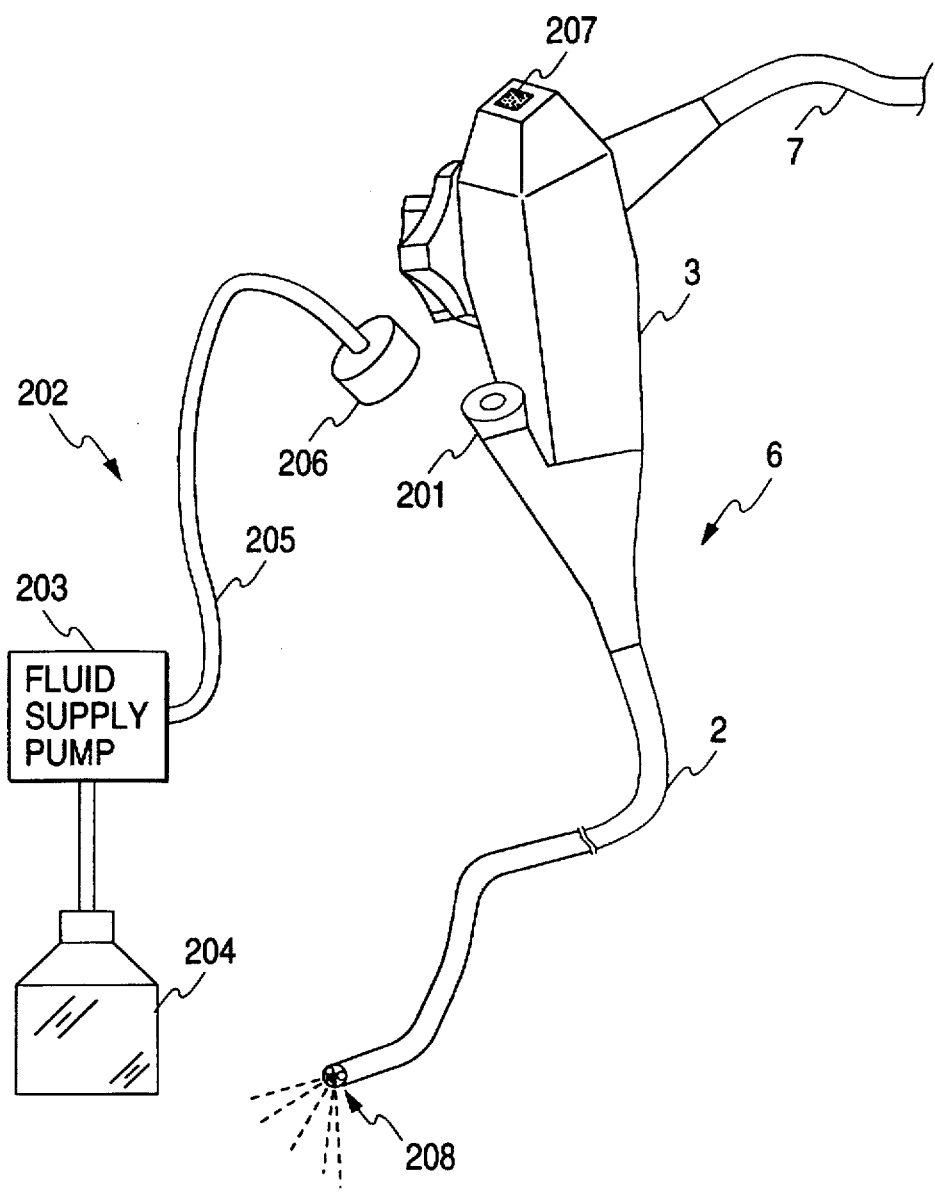
FIG. 36 shows the construction of an endoscope according to a sixteenth embodiment of the invention.

We now describe the sixteenth embodiment of the invention with specific reference to FIG. 36 which shows the composition of an endoscope according to the sixteenth embodiment.

The sixteenth embodiment is essentially the same as the first embodiment, so the following description concerns only the differences between the two embodiments and the components which are common to both embodiments are identified by like numerals and will not be described in detail.

The endoscope according to the sixteenth embodiment is generally indicated by 6 in FIG. 36 and differs from a conventional type in that it has a fluid supply member added for connection to a forceps channel port 201 which is commonly provided in the conventional type. The fluid supply member generally indicated by 202 is the combination of a fluid supply pump 203, a fluid supply tank 204, a fluid supply tube 205 and a socket 206. The fluid supply tank 204 is filled with a staining solution containing a dye such as a fluorescent agent which facilitates the reflection of the measuring light.

The other structural aspects of the sixteenth embodiment are identical to the first embodiment.

Prior to measuring the 3-D configuration of the object, socket 206 is coupled to the forceps channel port 201 and an operating switch 207 is depressed. The switch 207 need not necessarily be provided within the endoscope 6. When the switch is turned on, the fluid supply pump 203 is actuated and the staining solution in the fluid supply tank 204 flows through the fluid supply tube 205, the forceps channel port 201 and the forceps channel (not shown) to emerge from a forceps port 208 at the distal end such that it is sprayed over the object. Thus, the surface of the object is covered with the staining solution to provide ease in the reflection of the measuring light.

The other operational features of the sixteenth embodiment are the same as in the first embodiment. Since the measuring light is reflected with great ease, the sensitivity of optical detectors 1 to m and the gains of amplifiers 1 to m at a subsequent stage can be lowered to sufficiently lower values to reduce the noise and other unwanted components. This effect could be enhanced by using an infrared radiation rather than visible light as the measuring light since the absorption of light by the living body is suppressed.

Figure 37:
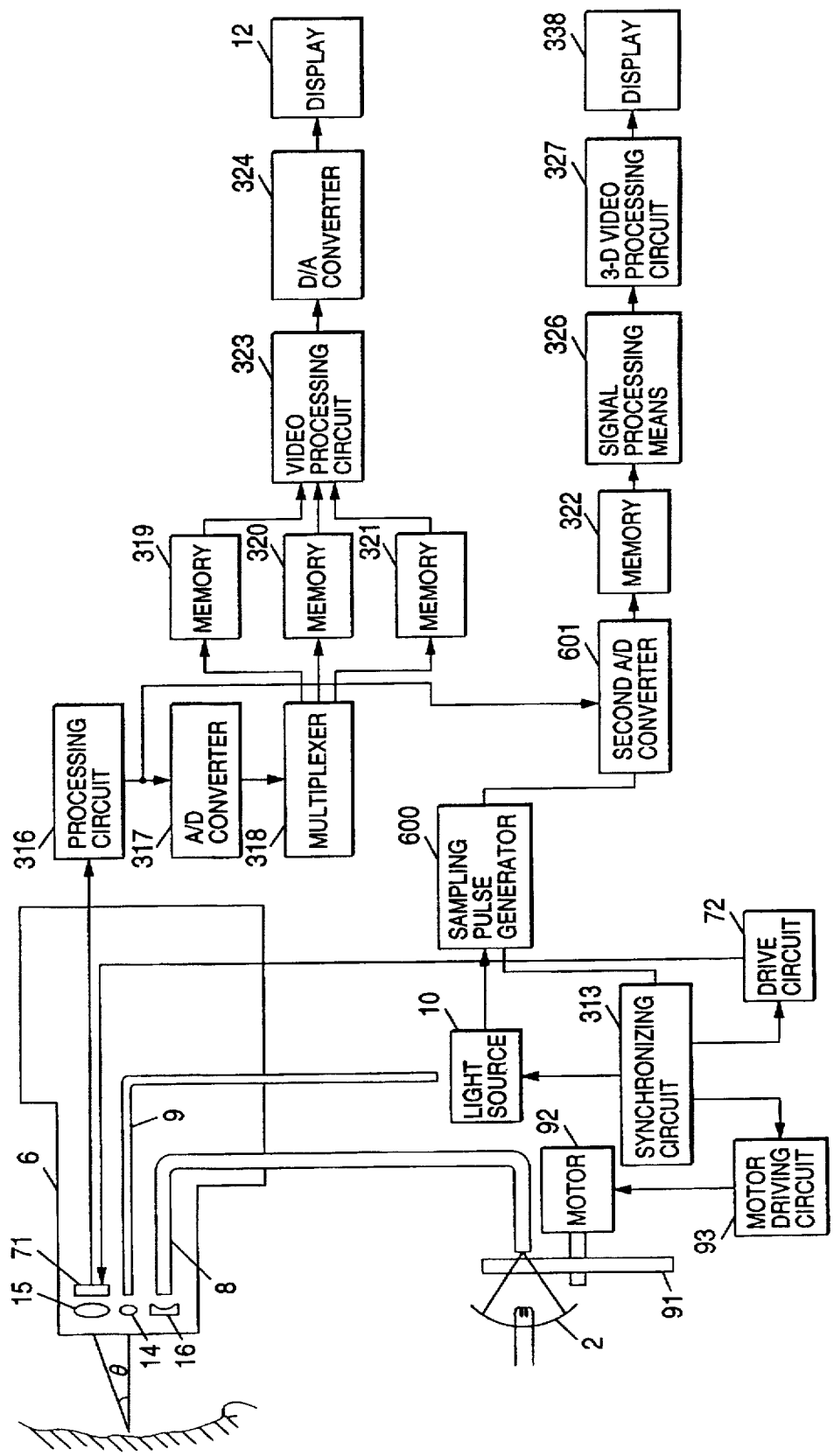
FIG. 37 is a block diagram showing the composition of a seventeenth embodiment of the invention.
Figure 38:
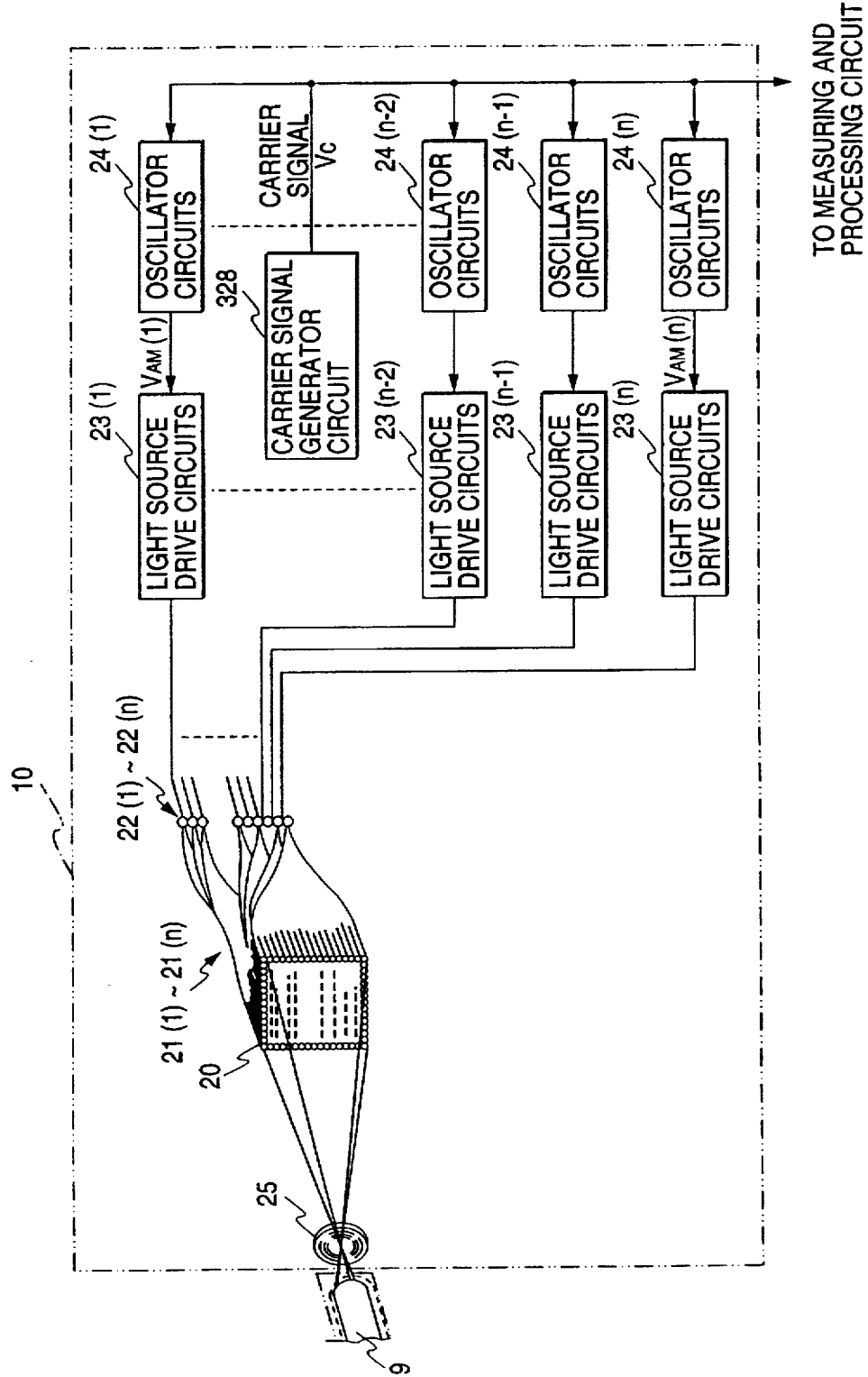
FIG. 38 shows the composition of a light source for projecting the measuring light as indicated by 10 in FIG. 37.
Figure 39:
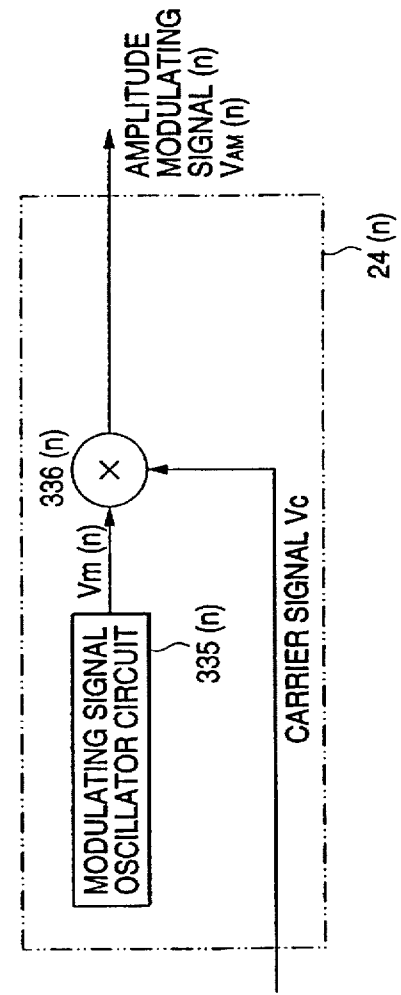
FIG. 39 shows the configuration of a modulator circuit indicated by 24 (n) in FIG. 38.
Figure 40:
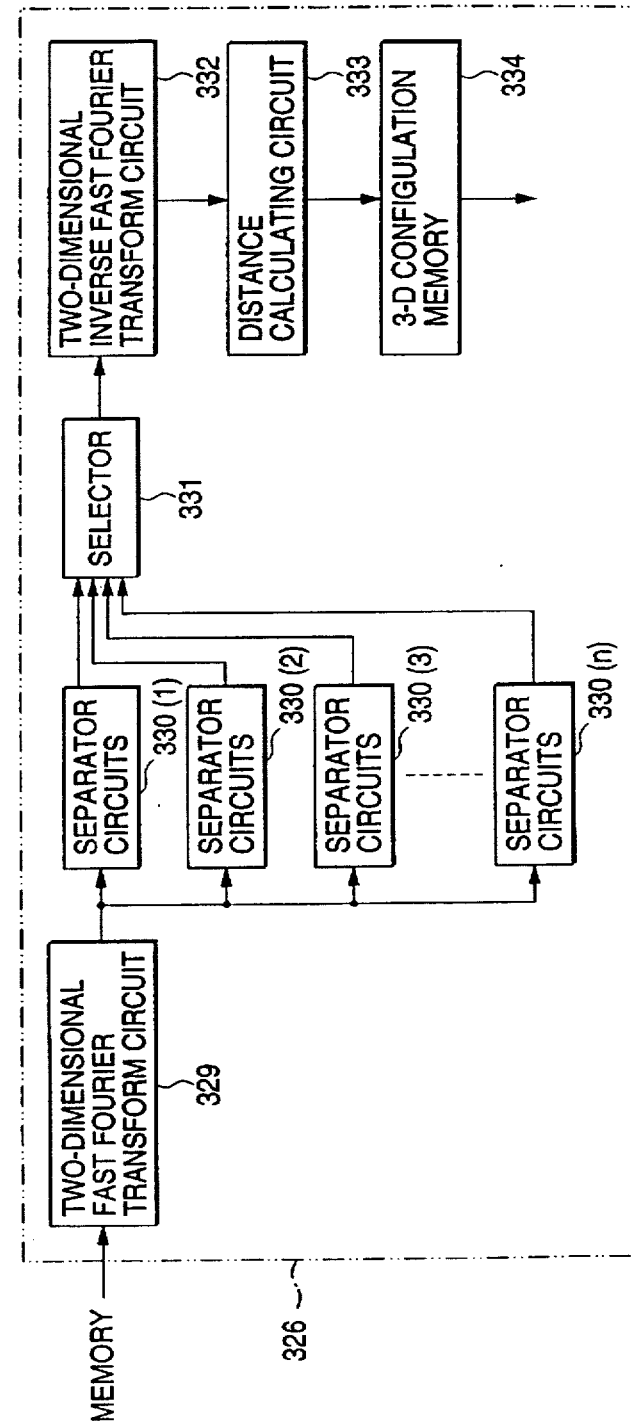
FIG. 40 shows the configuration of a measuring and processing circuit indicated by 326 in FIG. 37.
Figure 41:
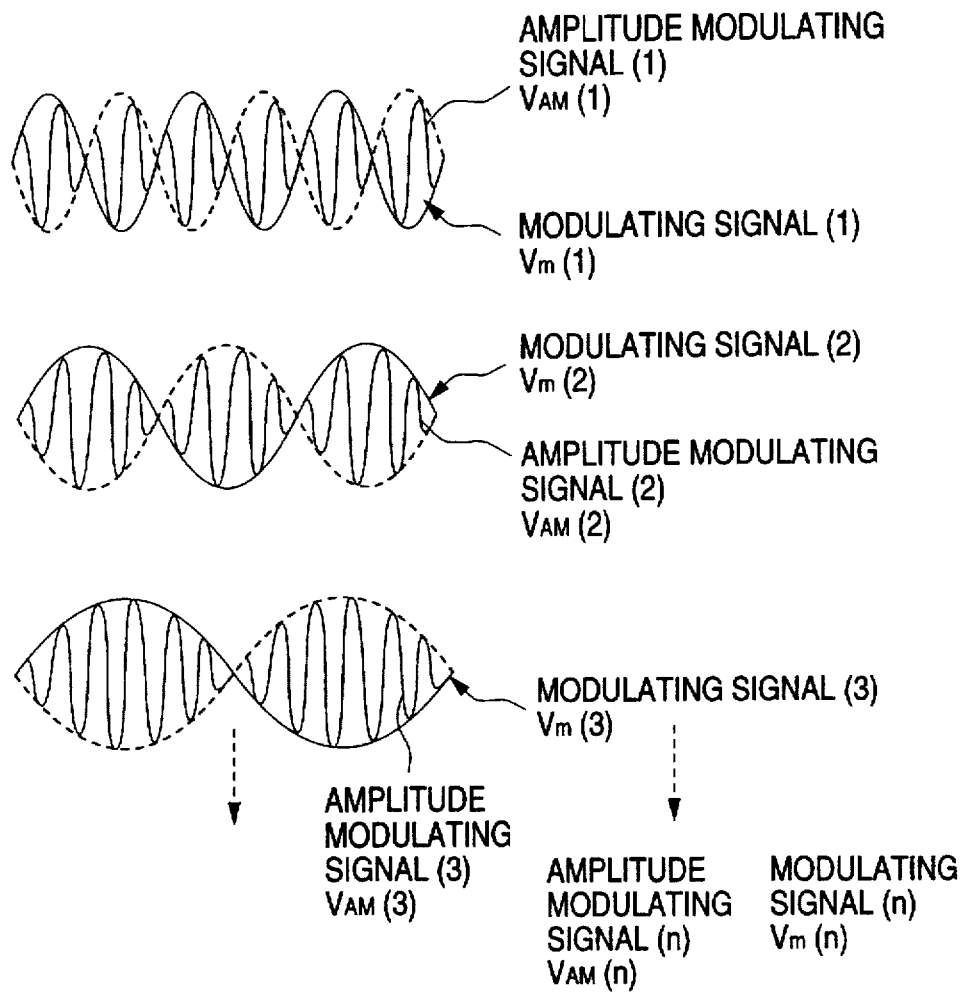
FIG. 41 illustrates carrier signal Vc, modulating signals Vm(n) and up-converted signals $V_{AM}(n)$ which are shown in FIG. 38.
Figure 42:
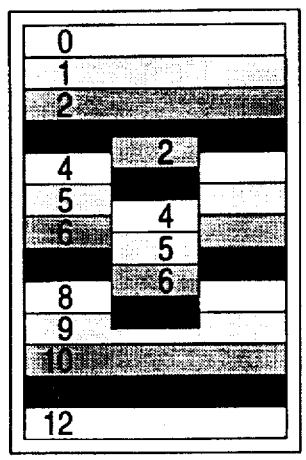
FIG. 42 illustrates the operating principle of the invention.

We then describe the seventeenth embodiment of the invention with reference to FIGS. 38 to 42, in which: FIG. 37 is a block diagram showing the composition of the seventeenth embodiment; FIG. 36 shows the composition of a light source for projecting the measuring light as indicated by 10 in FIG. 37; FIG. 39 shows the configuration of a modulator circuit indicated by 24(n) in FIG. 38; FIG. 40 shows the configuration of a measuring and processing circuit indicated by 326 in FIG. 37; FIG. 41 illustrates carrier signal Vc, modulating signal Vm(n) and up-converted signals $V_{AM}(n)$ which are shown in FIG. 38; and FIG. 42 illustrates the operating principle of the invention.

As shown in FIG. 37, the endoscope apparatus for measuring three-dimensional configurations comprises the following components: a viewing illumination light source 2; an endoscope unit 6; a viewing lightguide 8; a measuring lightguide 9; the measuring light projecting source 10; a measuring projection lens 14; an objective lens 15; a viewing illumination lens 16; a solid-state imaging device such as CCD 71; a circuit 72 for driving the solid-state imaging device 71; a rotating filter 91 that consists of a red, a green and blue light transmissive area and a light-opaque area and which is provided between the viewing illumination light source 2 and the viewing lightguide 8 in such a way that it is rotatable with a motor 92; a circuit 93 for driving the motor 92; a synchronizing circuit 313; a circuit 316 for amplifying and otherwise processing the output signal from the solid-state imaging device 71; and A/D converter 317; a multiplexer 318; memories 319 to 321 which are selectively supplied with signals from the multiplexer 318 that are obtained in synchronism with the rotation of the filter 91 in association with the illumination with red, green and blue light; a video processing circuit 323; a digital-to-analog converter (hereinafter referred to as D/A converter) 324; a sampling pulse generator 600 for generating periodic sequences of sampling pulses s(i) (i=1,2, . . . ,n) in a period of which sampling pulses are generated in synchronism with the carrier signal Vc as shown in FIG. 45; a second A/D converter 601 for sampling and analog-to-digital converting the fed object image formed by the measuring light; a measuring processing circuit 326 for calculating the surface state of the object from the signal stored in the frame memory 322; a 3-D video processing circuit 327 for describing a graphic representation of the three-dimensional configuration of the object (e.g. its bird's eye view or contour map) on the basis of the result of calculation; and a display 338 to be used as a monitor for displaying a 3-D measured image of the object.

As shown in FIG. 38, the light source 10 for projecting the measuring light comprises the following components: a plurality of optical fiber bundles 21(1) to 21(n) that are gathered at the entrance end and which are arranged parallel to each other at the exit end to form a flat plane 20; n light sources 22(1) to 22(n) which are typically composed of a semiconductor laser for admitting the measuring light into the entrance end face of each of the optical fiber bundles 21(1) to 21(n); light source drive circuits 23(1) to 23(n) for driving the respective light sources 22(1) to 22(n); modulator circuits 24(1) to 24(n) for supplying a drive signal to the respective light source drive circuits 23(1) to 23(n); and a carrier signal generator circuit 328 for supplying a carrier signal Vc to each of the modulator circuits 24(1) to 24(n).

As shown in FIGS. 39 and 41, the modulator circuits 24(1) to 24(n) are composed of modulating signal generating circuits 335(1) to 335(n) for generating modulating signals Vm(1) to Vm(n) at different frequencies and converting circuits 336(1) to 336(n) for converting the respective modulating signals Vm(1) to Vm(n) with the carrier signal Vc to produce up-converted signals $V_{AM}(1)$ to $V_{AM}(n)$.

As shown in FIG. 40, the measuring processing circuit 326 is composed of the following components: a two-dimensional FFT circuit 329 for Fourier transforming the one frame image (supplied from the frame memory 322) from spatial domain to spatial frequency domain (where resulting spectrum includes the frequency information corresponding to modulating signals Vm(1) to Vm(n) as well as the spatial shape of the object), spatial digital filters 330(1) to 330(n) for extracting the frequency components corresponding to the frequencies of the modulating signals Vm(1) to Vm(n) respectively; a selector 331 for reading output signals from the digital filters 330(1) to 330(n) in a selective and sequential manner; a two-dimensional IFFT circuit 332 for inverse-Fourier transforming each frequency component (extracted by the spatial digital filters 330(1) to 330(n)) from spatial frequency domain into spatial domain; a distance calculating circuit 333 for computing the departure from the reference position for each of the separated frequency components; and a 3-D configuration memory 334 for storing the results of computation with the distance calculation circuit 333 and representing them on the display.

Having the composition described in the preceding paragraphs, the seventeenth embodiment will operate as follows. The light issuing from the viewing illumination light source 2 is sequentially transformed to red, green and blue light or blocked as the filter 91 is rotated by the motor 92. The admitted light components are passed through the viewing lightguide 8 and the illumination lens 16 to illuminate the object. When the light-opaque area of the rotating filter 91 is inserted into the optical path, the measuring light projecting source 10 emits in response to the control signal from the synchronizing circuit 313 and the measuring light is projected onto the object via the measuring lightguide 9 and the measuring projection lens 14.

The measuring light is such that a plurality of lines of liner light having different modulation frequencies will be projected simultaneously by supplying the light source drive circuits 23(1) to 23(n) with up-converted signals $V_{AM}(1)$ to $V_{AM}(n)$ of different modulation frequencies that have been generated in the respective modulator circuits 24(1) to 24(n) and by controlling the emission from the light sources 22(1) to 22(n) with the drive circuits 23(1) to 23(n) in accordance with the supplied amplitude modulating signals $V_{AM}(1)$ to $V_{AM}(n)$.

The thus illuminated object is focused by the objective lens 15 and imaged on the solid-state imaging device 71. The measuring light illuminates the object in such a manner that each of the line-shaped lights is orthogonal to the horizontal line of the imaging device 71. In response to the control signal from the synchronizing circuit 313, the solid-state imaging device 71 is actuated by the drive circuit 72 in synchronism with the rotation of the filter 91, thereby producing successive signals on the object image formed by the red, green and blue light, as well as by the measuring light. It should be noted that the drive circuit 72 generates read-out pulses at much higher rate such that one frame of image is read in a moment between two neighboring sampling pulses S(i) and S(i+1) when the object is illuminated by the measuring light. These signals are amplified and otherwise processed by the processing circuit 316 before delivery to the A/D converter 317 and the second A/D converter 601. The signals fed into the A/D converter 317 are subjected to analog-to-digital conversion and the resulting digital signals are selectively supplied to the respective memories 319 to 321 according to the format determined by the multiplexer 318. Thus, the image signal for the red light is fed for storage in the memory 319; the image signal for the green light is fed for storage in the memory 320; and the image signal for the blue light is fed for storage in the memory 321. The image signals for ordinary viewing that have been stored in memories 319 to 321 are fed into the video processing circuit 323, where they are subjected to gamma correction, edge enhancement and other processing; the processed image signals are fed into the D/A converter 324 for digital-to-analog conversion, thereby producing a color image that is represented on the display 12.

Speaking of the signals fed into the second A/D converter 601, i-th (i=1,2,...,n) horizontal line of the solid-state imaging device 71 is sampled in synchronism with the sampling pulse S(i), converted into digital signal for storage in the frame memory 322. As a result, each of the vertical lines stored in the frame memory 322 carries the frequency information corresponding to each of modulating signals Vm(1) to Vm(n). The stored image signals due to the measuring light are then fed to the two-dimensional FFT circuit 329 for transformation from the spatial domain to the spatial frequency domain. The resulting signals in the frequency domain fed into the digital spatial filters 330(1) to 330(n), where they are separated into and held as signals of the frequency components corresponding to the modulating signals Vm(1) to Vm(n). The separated and held signals are read with the selector 331 in a selective and sequential manner as they are delivered from the digital filters 330(1) to 330(n); the signals are then fed into the two-dimensional IFFT circuits 332, where they are subjected to inverse fast Fourier transform so that they are transformed back to the spatial domain. One of these signals in such that as the result of projection onto the object, the shape of a single line of measuring line-shaped light has changed in accordance with the surface state of the object; hence, the signal of interest is equivalent to n lines of line-shaped light that have been projected onto the object simultaneously so as to change in shape. For a single line of line-shaped light, comparison with the preliminary measured and stored data on the reference position is made in the distance calculating circuit 333 to compute the surface state of the object; the calculated data for the surface state of the object that has been illuminated with the n lines of line-shaped light are stored in the 3-D configuration memory 334 and processed into a graphic representation of the 3-D configuration of the object in the 3-D video processing circuit 327, with the 3-D graphic image being represented on the display 338.

In the seventeenth embodiment of the invention, more than one measuring light that has been encoded at different amplitude modulation frequencies is projected onto the object simultaneously and the reflected light from the object is separated into signals of the respective frequency components, which are then subjected to the necessary processing. Hence, compared to the prior art methods of measurement such as one involving the scanning of slit light with a mirror and the spatial coding method in which the object is sequentially illuminated with a plurality of patterns of coded light that are created by turning slit light on and off in the presence of a polygonal mirror, the seventeenth embodiment of the invention which has no mirror mechanism allows the three-dimensional configuration of the object to be measured in a by far more compact and faster way at a higher resolution.

In the foregoing description of the seventeenth embodiment, the modulator circuits are assumed to perform amplitude modulation but this is not the sole case of the invention and other methods of modulation may be adopted such as frequency or phase modulation.

As described on the foregoing pages, the apparatus of the invention for measuring three-dimensional configurations is such that the means for projecting the measuring light spatially separates the more than one measuring light from the measuring light generating means for projecting said light onto the surface to be measured of the object, and the means for analyzing the reflected light from the surface to be measured differentiates the reflected components of the more than one measuring light on the basis of the modulation frequencies with respect to the spatial distribution of the reflected light sensed by the detection means, and the distance calculating means calculates the distance between each point in the surface to be measured and the measuring light projecting means from the spatial position of each of the reflected components differentiated by the reflected light analyzing means. This procedure offers the advantage that many kinds of measuring (line-shaped) light can be projected onto the object simultaneously so as to improve the measuring speed and the resolution at the same time.

What is claimed is:

1. An endoscope apparatus for measuring three-dimensional configurations comprising:

measuring light generating means (23, 24, and 22) for generating simultaneously a plurality of measuring lights at different modulation frequencies;

measuring light projecting means (20, 25, 9, and 14) for spatially separating said plurality of measuring lights such that they are projected simultaneously onto the whole surface of an object to be measured;

light receiving means (11) for receiving the measuring lights reflected from the object;

signal processing means (35 and 326) that preliminarily stores specific distance position information which is supplied with an output signal from said light receiving means to derive the distance to the object, wherein said signal processing means (35 and 326) has a plurality of separator circuits (42 or 53) for separating frequency components from the output signal from said light receiving means (11); a plurality of peak position detector circuits (43) coupled to output terminals of said separator circuits and which are supplied with outputs of the separator circuits operating at a same center frequency, a distance calculating circuit (44) coupled to said peak position detector circuits, and a three-dimensional configuration memory (45) coupled to said distance calculating circuit, said distance calculating circuit storing specific distance position information; and an endoscope unit (6) that transmits the measuring light from said measuring light generating means to the object and which transmits the reflected lights from the object to said light receiving means.

2. An endoscope apparatus according to claim 1, wherein said measuring light generating means has a plurality of oscillator circuits (24) operating at different frequencies, a plurality of light source drive circuits (23) coupled respectively to said oscillator circuits, and a light source (22, 173 182) coupled to each of said light source drive circuits.

3. An endoscope apparatus according to claim 1, wherein said measuring light generating means has a surface illuminant (47), a spatial optical modulator (48) provided in front of said surface illuminant, and a drive circuit (49) coupled to said spatial optical modulator.

4. An endoscope apparatus according to claim 2, wherein said measuring light projecting means has a plurality of light transmitting members (21) that are gathered at the entrance end and arranged parallel to each other at the exit end to form a flat plane (20), and an imaging lens (25) provided in front of said flat plane.

5. An endoscope apparatus according to claim 2, wherein said measuring light projecting means has a light transmitting member (151) the first end face of which consists of individually separated elements and provided in front of said light source whereas the second end consists of linearly aligned elements, and a cylindrical lens (152) provided in front of the second end of said light transmitting member.

6. An endoscope apparatus according to claim 2, wherein said measuring light projecting means has a plurality of light transmitting elements (21) that couple said light source directly to a measuring light transmitting image guide fiber (9) in said endoscope unit.

7. An endoscope apparatus according to claim 1, which further includes measuring light's position detecting means (33) and (34) for accepting the measuring light reflected from the object, the output of said measuring light's position detecting means being fed into said signal processing means.

8. An endoscope apparatus according to claim 7, which further includes light-receiving member scanning means (36 or 121 or 131 and 132), with said measuring light's position detecting means having a light receiving member (33).

9. An endoscope apparatus according to claim 8, wherein said light receiving member (33) consists of linearly aligned elements of said light-receiving member scanning means.

10. An endoscope apparatus according to claim 8, wherein said light-receiving member scanning means has a voice coil.

11. An endoscope apparatus according to claim 8, wherein said light-receiving member scanning means has a piezo-electric device.

12. An endoscope apparatus according to claim 7, wherein an electro-optical deflector (121) is provided in front of said measuring light's position detecting means.

13. An endoscope apparatus according to claim 7, wherein a transparent medium (131) and a heater (132) are provided in front of said measuring light's position detecting means.

14. An endoscope apparatus according to claim 7, wherein said measuring light's position detecting means has a spatial optical modulator (141) and a photodiode array (142).

15. An endoscope apparatus according to claim 1, which further includes first representation means (12) for representing a three-dimensional image as created by signal processing with said signal processing means.

16. An endoscope apparatus according to claim 1, which further includes an optical path splitting member (31) for splitting the optical path of the measuring light.

17. An endoscope apparatus according to claim 16, wherein one of the optical paths emerging from said optical path splitting member (31) is transmitted toward said signal processing means and the other path is transmitted to an eyepiece lens (32).

18. An endoscope apparatus according to claim 16, wherein one of the optical paths emerging from said optical path splitting member is transmitted toward said signal processing means and the other path is transmitted to video processing means (71, 72, 73 and 74), the output of which is transmitted to said signal processing means.

19. An endoscope apparatus according to claim 18, wherein said video processing means has an imaging device (71), an imaging device drive circuit (72), a video circuit (73) and an A/D converter (74).

20. An endoscope apparatus according to claim 19, wherein said imaging device has a CCD.

21. An endoscope apparatus according to claim 18, wherein said signal processing circuit has a 3-D image detecting circuit (111) and a 2-D image detecting circuit (112).

22. An endoscope apparatus according to claim 16, which further includes viewing light generating means (27, 28 and 26) and wherein said measuring light contains invisible light and a visible light transmissive filter (101) is provided at the first exit end of said optical path splitting member whereas an invisible light transmissive filter (102) is provided at the second exit end of said optical path splitting member.

23. An endoscope apparatus according to claim 16, wherein a spot light position detecting means (185) is provided between said optical path splitting member and said light receiving means.

24. An endoscope apparatus according to claim 23, wherein said spot light position detecting means has a horizontal position detecting fiber (191), a horizontal position light-shielding member (192), a vertical position detecting fiber (194) and a vertical position light-shielding member (195), said horizontal position detecting fiber being crossed with said vertical position detecting fiber at right angles.

25. An endoscope apparatus according to claim 1, wherein said measuring light generating means and said measuring light projecting means are provided within the light source unit (10) whereas said light receiving means and said signal processing means are provided within a measuring unit (11).

26. An endoscope apparatus according to claim 1, wherein said measuring light generating means, said measuring light projecting means, said light receiving means and said signal processing means are provided within a measuring unit (11).

27. An endoscope apparatus according to claim 26, which further includes a first and a second optical path splitting member (31 and 83) for splitting the reflected measuring light and wherein one of the optical paths emerging from the first optical path splitting member is transmitted to a first imaging device (71) and one of the optical paths emerging from the second optical path splitting member is transmitted to a second imaging device (85), with the outputs of the first and second imaging devices being fed into an image signal processor (87).

28. An endoscope apparatus according to claim 27, wherein the output of said image signal processor is fed into a second display unit (88).

29. An endoscope apparatus according to claim 1, which further includes viewing light generating means (27, 28 and 26).

30. An endoscope apparatus according to claim 29, wherein said viewing light generating means has a rotating filter (91) for applying R, G and B light successively.

31. An endoscope apparatus according to claim 30, which further includes a shutter (95) provided in front of the light receiving means.

32. An endoscope apparatus according to claim 1, wherein said separator circuits have filters (42).

33. An endoscope apparatus according to claim 1, wherein said separator circuits have fast Fourier transform circuits (53).

34. An apparatus endoscope according to claim 1, wherein said measuring light generating means has a modulating signal oscillator circuit (335) for generating a plurality of modulating signals at different frequencies, a carrier signal generator circuit (328) coupled to said modulating signal oscillator circuit, and an integrating circuit (336) that is supplied with the outputs of said modulating signal oscillator circuit and said carrier signal generator circuit and which produces an up-converted signal as an output.

35. An endoscope apparatus according to claim 34, wherein said signal processing means (326) has a two-dimensional fast Fourier transform circuit (329), a plurality of separator circuits (330) for separating frequency components from the output signals from said light receiving means, a selector (331) coupled to the output terminal of said separator circuits for reading output signals from said output terminals in a selective and sequential manner, a two-dimensional inverse fast Fourier transform circuit (332) coupled to the output terminal of said selector, a distance calculating circuit (333) coupled to the output terminal of said inverse fast Fourier transform circuit, and a 3-D configuration memory (334), said distance calculating circuit storing position information on said specified distance.

36. An endoscope apparatus according to claim 35, wherein said separator circuits have digital filters (330).

37. An endoscope apparatus according to claim 34, which further includes viewing light generating means (93, 92 and 91), said viewing light generating means has a rotating filter (91) for applying R, G and B light sequentially.

38. An endoscope apparatus according to claim 34, wherein said endoscope unit has a scope characteristics memory circuit (51), the output of which is fed into said signal processing means.

39. An endoscope apparatus according to claim 1, which further includes a light source unit characteristics memory circuit (61), the output of which is fed into said signal processing means.

40. An endoscope apparatus according to claim 1, wherein the modulation frequencies of said measuring light are intensity-modulated.

41. An endoscope apparatus according to claim 1, wherein the modulation frequencies of said measuring light have a carrier frequency.

42. An endoscope apparatus according to claim 1, wherein said signal processing means derives the distance to the object for each kind of said more than one measuring light having different modulation frequencies.

43. An endoscope apparatus according to claim 1, wherein said endoscope unit has fluid supply means (202, 203, 204, 205 and 206) for supplying a fluid that enhances the reflection of the measuring light.

44. A system for measuring three-dimensional configurations comprising:

measuring light generating means (23, 24, and 22) for generating simultaneously a plurality of measuring lights at different modulation frequencies;

measuring light projecting means 20, 25, 9, and 14 for spatially separating a plurality of measuring lights such that it is projected simultaneously onto the whole surface of an object to be measured;

light receiving means (11) for receiving the measuring lights reflected from the object;

signal processing means (35 and 326) that preliminarily stores specific distance position information which is supplied with an output signal from said light receiving means to derive the distance to the object, wherein said signal processing means (35 and 326) has a plurality of separator circuits (42 or 53) for separating frequency components from the output signal from said light receiving means (11);

a plurality of peak position detector circuits (43) coupled to output terminals of said separator circuits and which are supplied with outputs of the separator circuits operating at a same center frequency, a distance calculating circuit (44) coupled to said peak position detector circuits, and a three-dimensional configuration memory (45) coupled to said distance calculating circuit, said distance calculating circuit storing specific distance position information; and transmission means (6) that transmits the measuring lights from said measuring light generating means to the object and which transmits the reflected light from the object to said light receiving means.

45. A system according to claim 44, wherein said measuring light generating means has a plurality of oscillator circuits (24) operating at different frequencies, a plurality of light source drive circuits (23) coupled respectively to said oscillator circuits, and a light source (22, 173 and 182) coupled to each of said light source drive circuits.

46. A system according to claim 45, wherein said measuring light projecting means has a plurality of light transmitting members (21) that are gathered at the entrance end and arranged parallel to each other at the exit end to form a flat plane (20), and an imaging lens (25) provided in front of said flat plane.

47. A system according to claim 45, wherein said measuring light projecting means has a light transmitting member (151) the first end face of which consists of individually separated elements and provided in front of said light source whereas the second end consists of linearly aligned elements, and a cylindrical lens (152) provided in front of the second end of said light transmitting member.

48. A system according to claim 45, wherein said measuring light projecting means has a plurality of light transmitting elements (21) that couple said light source directly to a measuring light-transmitting image guide fiber (9) in said transmission means.

49. A system according to claim 44, wherein said measuring light generating means has a surface illuminant (47), a spatial optical modulator (48) provided in front of said surface illuminant, and a drive circuit 49 coupled to said spatial optical modulator.

50. A system according to claim 44, which further includes measuring light's position detecting means (33 and 34) for accepting the measuring light reflected from the object, the output of said measuring light's position detecting means being fed into said signal processing means.

51. An endoscope apparatus according to claim 50, which further includes light-receiving member scanning means (36 or 121 or 131 and 132), with said measuring light's position detecting means having a light receiving member (33).

52. A system according to claim 51, wherein said light receiving member (33) consists of linearly aligned elements on said light-receiving member scanning means.

53. A system according to claim 51, wherein said light-receiving member scanning means has a voice coil.

54. A system according to claim 51, wherein said light-receiving member scanning means has a piezoelectric device.

55. A system according to claim 51, wherein an electro-optical deflector (121) is provided in front of said measuring light's position detecting means.

56. A system according to claim 50, wherein a transparent medium (131) and a heater (132) are provided in front of said measuring light's position detecting means.

57. A system according to claim 50, wherein said measuring light's position detecting means has a spatial optical modulator (141) and a photodiode array (142).

58. A system according to claim 44, which further includes first representation means (12) for representing a three-dimensional image as created by signal processing with said signal processing means.

59. A system according to claim 44, which further includes an optical path splitting member (31) for splitting the optical path of the measuring light.

60. A system according to claim 59, wherein one of the optical paths emerging from said optical path splitting member (31) is transmitted toward said signal processing means and the other path is transmitted to an eyepiece lens (32).

61. A system according to claim 59, wherein one of the optical paths emerging from said optical path splitting member is transmitted toward said signal processing means and the other path is transmitted to video processing means (71, 72, 73 and 74), the output of which is transmitted to said signal processing means.

62. A system according to claim 61, wherein said video processing means has an imaging device (71), an imaging device drive circuit (72), a video circuit (73) and an A/D converter (74).

63. A system according to claim 61, wherein said signal processing circuit has a 3-D image detecting circuit (111) and a 2-D image detecting circuit (112).

64. A system according to claim 59, wherein a visible light transmissive filter (101) is provided at the first exit end of said optical path splitting member whereas an invisible light transmissive filter (102) is provided at the second exit end of said optical path splitting member.

65. A system according to claim 59, wherein a spot light position detecting means (185) is provided between said optical path splitting member ad said light receiving means.

66. A system according to claim 65, wherein said spot light position detecting means has a horizontal position detecting fiber (191), a horizontal position light-shielding member (192), a vertical position detecting fiber (194) and a vertical position light-shielding member (195), said horizontal position detecting fiber being crossed with said vertical position detecting fiber at right angles.

67. A system according to claim 44, wherein said measuring light generating means and said measuring light projecting means are provided within the light source unit (10) whereas said light receiving means and said signal processing means are provided within a measuring unit (11).

68. A system according to claim 67, wherein said imaging device has a CCD.

69. A system according to claim 44, wherein said measuring light generating means, said measuring light projecting means, said light receiving means and said signal processing means are provided within a measuring unit (11).

70. A system according to claim 69, which further includes a first and a second optical path splitting member (31) and (83) for splitting the reflected measuring light and wherein one of the optical paths emerging from the first optical path splitting member is transmitted to a first imaging device (71) and one of the optical paths emerging from the second optical path splitting member is transmitted to a second imaging device (85), with the outputs of the first and second imaging devices being fed into an image signal processor (87).

71. A system according to claim 70, wherein the output of said image signal processor is fed into a second display unit (88).

72. A system according to claim 44, which further includes viewing light generating means (27, 28 and 26).

73. A system according to claim 72, wherein said viewing light generating means has a rotating filter (91) for applying R, G and B light successively.

74. A system according to claim 73, which further includes a shutter (95) provided in front of the light receiving means.

75. A system according to claim 44, wherein said separator circuits have filters (42).

76. A system according to claim 46, wherein said separator circuits have fast Fourier transform circuits (53).

77. A system according to claim 44, wherein said transmission means has an endoscope unit (6).

78. A system according to claim 77, wherein said endoscope unit has a scope characteristics memory circuit (51), the output of which is fed into said signal processing means.

79. A system according to claim 44, which further includes a light source unit characteristics memory circuit (61), the output of which is fed into said signal processing means.

80. A system according to claim 44, wherein said measuring light generating means has a modulating signal oscillator circuit (335) for generating a plurality of modulating signals at different frequencies, a carrier signal generator circuit (328) coupled to said modulating signal oscillator circuit, and an up-converting circuit (336) that is supplied with the outputs of said modulating signal oscillator circuit and said carrier signal generator circuit and which produces an up-converted signal as an output.

81. A system according to claim 80, wherein said signal processing means (326) has a two-dimensional fast Fourier transform circuit (329), a plurality of separator circuits (330) for separating frequency components from the output signals from said light receiving means, a selector (331) coupled to the output terminals of said separator circuits for reading output signals from said output terminals in a selective and sequential manner, a two-dimensional inverse fast Fourier transform circuit (332) coupled to the output terminal of said selector, a distance calculating circuit (333) coupled to the output terminal of said two-dimensional inverse fast Fourier transform circuit, and a 3-D configuration memory (334), said distance calculating circuit storing position information on said specified distance.

82. A system according to claim 81, wherein said separator circuits have digital filters (330).

83. A system according to claim 80, which further includes viewing light generating means (93, 92 and 91), said viewing light generating means has a rotating filter (91) for applying R, G and B light sequentially.

84. A system according to claim 44, wherein the modulation frequencies of said measuring light are intensity-modulated.

85. A system according to claim 44, wherein the modulation frequencies of said measuring light have a carrier frequency.

86. A system according to claim 44, wherein said signal processing means derives the distance to the object for each kind of said more than one measuring light having different modulation frequencies.

87. A system according to claim 44, wherein said transmission means has fluid supply means (202, 203, 204, 205 and 206) for supplying a fluid that enhances the reflection of the measuring light.

* * * * *

UNITED STATES PATENT AND TRADEMARK OFFICE
CERTIFICATE OF CORRECTION

PATENT NO. : 5,784,098
DATED : July 21, 1998
INVENTOR(S) : Shoji et al.

It is certified that error appears in the above-identified patent and that said Letters Patent is hereby corrected as shown below:

Column 27, Line 48, change "claim 34" to --claim 1--.

Column 28, Line 8, change "20, 25, 9, and 14" to --(20, 25, 9, and 14)--;

Line 64, change "49" to --(49)--.

Signed and Sealed this

Nineteenth Day of January, 1999

Attest:

Attesting Officer

*Acting Commissioner of Patents and Trademarks*